(12) United States Patent
Kim et al.

(10) Patent No.: US 9,271,788 B2
(45) Date of Patent: Mar. 1, 2016

(54) ABLATION DEVICES WITH ADJUSTABLE RADIATING SECTION LENGTHS, ELECTROSURGICAL SYSTEMS INCLUDING SAME, AND METHODS OF ADJUSTING ABLATION FIELDS USING SAME

(71) Applicant: Covidien LP, Mansfield, MA (US)

(72) Inventors: Steven Kim, Los Altos, CA (US);
Kenlyn S. Bonn, Lakewood, CO (US);
Mani N. Prakash, Boulder, CO (US);
Francesca Rossetto, Longmont, CO (US)

(73) Assignee: Cividien LP, Mansfield, MA (US)

( * ) Notice: Subject to any disclaimer, the term of this patent is extended or adjusted under 35 U.S.C. 154(b) by 312 days.

(21) Appl. No.: 13/853,363

(22) Filed: Mar. 29, 2013

(65) Prior Publication Data
US 2013/0231653 A1  Sep. 5, 2013

Related U.S. Application Data

(63) Continuation of application No. 12/732,508, filed on Mar. 26, 2010, now Pat. No. 8,409,188.

(51) Int. Cl.
*A61B 18/18* (2006.01)

(52) U.S. Cl.
CPC .............. *A61B 18/18* (2013.01); *A61B 18/1815* (2013.01); *A61B 2018/1861* (2013.01)

(58) Field of Classification Search
CPC ............... A61B 18/18; A61B 18/1815; A61B 2018/1861; A61B 2018/1869
See application file for complete search history.

(56) References Cited

U.S. PATENT DOCUMENTS

| | | |
|---|---|---|
| D223,367 S | 4/1972 | Kountz |
| 4,041,498 A | 8/1977 | Freimark et al. |
| D263,020 S | 2/1982 | Rau, III |
| D266,842 S | 11/1982 | Villers et al. |
| D278,306 S | 4/1985 | McIntosh |
| 4,674,481 A | 6/1987 | Boddie, Jr. et al. |
| D295,893 S | 5/1988 | Sharkany et al. |
| D295,894 S | 5/1988 | Sharkany et al. |
| 5,314,466 A * | 5/1994 | Stern et al. ............ 607/156 |
| D354,218 S | 1/1995 | Van de Peer |
| 5,389,098 A | 2/1995 | Tsuruta et al. |
| 5,403,311 A | 4/1995 | Abele et al. |
| 5,405,346 A * | 4/1995 | Grundy et al. ............ 606/41 |
| 5,683,384 A | 11/1997 | Gough et al. |

(Continued)

FOREIGN PATENT DOCUMENTS

| | | |
|---|---|---|
| CN | 1103807 A | 6/1995 |
| DE | 390937 C | 3/1924 |

(Continued)

OTHER PUBLICATIONS

Extended European Search Report from Appl. No. EP 14181008.5 dated Feb. 5, 2015.

(Continued)

*Primary Examiner* — Michael Peffley

(57) ABSTRACT

An energy applicator for directing energy to tissue includes a feedline and a radiating section operably coupled to the feedline, wherein the radiating section has a length. The energy applicator also includes a length adjustment member adapted to allow for selective adjustment of the length of the radiating section.

9 Claims, 11 Drawing Sheets

(56) References Cited

U.S. PATENT DOCUMENTS

| | | | |
|---|---|---|---|
| 5,792,165 A | 8/1998 | Klieman et al. | |
| 5,800,494 A | 9/1998 | Campbell et al. | |
| 6,016,452 A | 1/2000 | Kasevich | |
| D424,693 S | 5/2000 | Pruter | |
| D424,694 S | 5/2000 | Tetzlaff et al. | |
| D425,201 S | 5/2000 | Tetzlaff et al. | |
| 6,197,024 B1 | 3/2001 | Sullivan | |
| 6,241,725 B1 | 6/2001 | Cosman | |
| 6,277,083 B1 | 8/2001 | Eggers et al. | |
| D449,886 S | 10/2001 | Tetzlaff et al. | |
| 6,312,428 B1 | 11/2001 | Eggers et al. | |
| 6,322,559 B1 | 11/2001 | Daulton et al. | |
| 6,325,796 B1 | 12/2001 | Berube et al. | |
| 6,355,034 B2 | 3/2002 | Cosmescu | |
| D457,958 S | 5/2002 | Dycus et al. | |
| D457,959 S | 5/2002 | Tetzlaff et al. | |
| 6,575,969 B1 | 6/2003 | Rittman, III et al. | |
| D487,039 S | 2/2004 | Webster et al. | |
| D496,997 S | 10/2004 | Dycus et al. | |
| 6,802,840 B2* | 10/2004 | Chin et al. | 606/41 |
| D499,181 S | 11/2004 | Dycus et al. | |
| 6,878,147 B2 | 4/2005 | Prakash et al. | |
| 6,918,907 B2 | 7/2005 | Kelly et al. | |
| 6,974,455 B2* | 12/2005 | Garabedian | A61B 18/1482 606/41 |
| D525,361 S | 7/2006 | Hushka | |
| 7,112,199 B2 | 9/2006 | Cosmescu | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| 7,311,703 B2* | 12/2007 | Turovskiy et al. | 606/33 |
| 7,326,206 B2 | 2/2008 | Paul et al. | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,863,984 B1 | 1/2011 | Behnke | |
| D634,010 S | 3/2011 | DeCarlo | |
| 7,998,139 B2 | 8/2011 | Rossetto et al. | |
| 8,012,148 B2 | 9/2011 | Turovskiy et al. | |
| 8,035,570 B2 | 10/2011 | Prakash et al. | |
| 8,038,693 B2 | 10/2011 | Allen | |
| 8,118,808 B2 | 2/2012 | Smith et al. | |
| 8,197,473 B2 | 6/2012 | Rossetto et al. | |
| 8,202,270 B2 | 6/2012 | Rossetto et al. | |
| 8,216,227 B2 | 7/2012 | Podhajsky | |
| 8,235,981 B2 | 8/2012 | Prakash et al. | |
| 8,251,987 B2 | 8/2012 | Willyard | |
| 8,282,632 B2 | 10/2012 | Rossetto | |
| 8,292,881 B2 | 10/2012 | Brannan et al. | |
| 8,317,703 B2 | 11/2012 | Brannan | |
| 8,328,799 B2 | 12/2012 | Brannan | |
| 8,328,800 B2 | 12/2012 | Brannan | |
| 8,328,801 B2 | 12/2012 | Brannan | |
| 8,334,812 B2 | 12/2012 | Brannan | |
| 8,343,145 B2 | 1/2013 | Brannan | |
| 8,353,903 B2 | 1/2013 | Podhajsky | |
| 8,355,803 B2 | 1/2013 | Bonn et al. | |
| 8,382,750 B2 | 2/2013 | Brannan | |
| 8,394,086 B2 | 3/2013 | Behnke et al. | |
| 8,394,087 B2 | 3/2013 | Willyard et al. | |
| 8,394,092 B2 | 3/2013 | Brannan | |
| 8,409,187 B2 | 4/2013 | Bonn | |
| 8,409,188 B2 | 4/2013 | Kim | |
| 8,430,871 B2 | 4/2013 | Brannan | |
| 2003/0073988 A1 | 4/2003 | Berube et al. | |
| 2004/0181216 A1 | 9/2004 | Kelly et al. | |
| 2007/0049917 A1* | 3/2007 | Yang | A61B 18/18 606/33 |
| 2007/0078453 A1 | 4/2007 | Johnson et al. | |
| 2007/0088354 A1 | 4/2007 | Sugita | |
| 2007/0270895 A1 | 11/2007 | Nobis et al. | |
| 2008/0221650 A1 | 9/2008 | Turner et al. | |
| 2009/0118727 A1 | 5/2009 | Pearson et al. | |
| 2009/0131926 A1* | 5/2009 | Rusin et al. | 606/33 |
| 2009/0306656 A1 | 12/2009 | Desinger et al. | |
| 2010/0057070 A1 | 3/2010 | Behnke et al. | |
| 2010/0076422 A1 | 3/2010 | Podhajsky | |
| 2010/0087808 A1 | 4/2010 | Paulus | |
| 2010/0092939 A1 | 4/2010 | Belous et al. | |
| 2010/0094272 A1 | 4/2010 | Rossetto et al. | |
| 2010/0094273 A1 | 4/2010 | Rossetto et al. | |
| 2010/0097284 A1 | 4/2010 | Brannan et al. | |
| 2010/0256624 A1 | 10/2010 | Brannan et al. | |
| 2010/0262134 A1 | 10/2010 | Jensen et al. | |
| 2010/0286681 A1 | 11/2010 | Podhajsky | |
| 2010/0286683 A1 | 11/2010 | Podhajsky | |
| 2010/0305559 A1 | 12/2010 | Brannan et al. | |
| 2010/0305560 A1 | 12/2010 | Peterson | |
| 2010/0321192 A1 | 12/2010 | Brannan | |
| 2010/0321257 A1 | 12/2010 | Brannan | |
| 2010/0331834 A1 | 12/2010 | Peterson et al. | |
| 2011/0034913 A1 | 2/2011 | Brannan | |
| 2011/0034917 A1 | 2/2011 | Brannan | |
| 2011/0034919 A1 | 2/2011 | DeCarlo | |
| 2011/0040300 A1 | 2/2011 | Brannan | |
| 2011/0046621 A1 | 2/2011 | Poshajsky | |
| 2011/0054458 A1 | 3/2011 | Behnke | |
| 2011/0054459 A1 | 3/2011 | Peterson | |
| 2011/0060325 A1 | 3/2011 | Bonn | |
| 2011/0060326 A1 | 3/2011 | Smith et al. | |
| 2011/0066144 A1 | 3/2011 | Bonn et al. | |
| 2011/0071511 A1 | 3/2011 | Brannan et al. | |
| 2011/0071512 A1 | 3/2011 | Behnke, II et al. | |
| 2011/0071582 A1 | 3/2011 | Willyard et al. | |
| 2011/0073594 A1 | 3/2011 | Bonn | |
| 2011/0077633 A1 | 3/2011 | Bonn et al. | |
| 2011/0077634 A1 | 3/2011 | Brannan | |
| 2011/0077635 A1 | 3/2011 | Bonn | |
| 2011/0077636 A1 | 3/2011 | Brannan et al. | |
| 2011/0077637 A1 | 3/2011 | Brannan | |
| 2011/0077638 A1 | 3/2011 | Brannan | |
| 2011/0077639 A1 | 3/2011 | Brannan et al. | |
| 2011/0098695 A1 | 4/2011 | Brannan | |
| 2011/0098696 A1 | 4/2011 | Brannan | |
| 2011/0098697 A1 | 4/2011 | Brannan | |
| 2011/0118721 A1 | 5/2011 | Brannan | |
| 2011/0118731 A1 | 5/2011 | Ladtkow | |
| 2011/0213351 A1 | 9/2011 | Lee et al. | |
| 2011/0238054 A1 | 9/2011 | Kim et al. | |
| 2011/0238055 A1 | 9/2011 | Kim et al. | |
| 2012/0172860 A1 | 7/2012 | Brannan | |
| 2012/0172861 A1 | 7/2012 | Brannan | |
| 2012/0172862 A1 | 7/2012 | Brannan | |
| 2012/0172863 A1 | 7/2012 | Brannan | |
| 2012/0215103 A1 | 8/2012 | Brannan | |
| 2012/0215104 A1 | 8/2012 | Brannan | |
| 2012/0232544 A1 | 9/2012 | Willyard et al. | |
| 2012/0232549 A1 | 9/2012 | Willyard et al. | |
| 2013/0030429 A1 | 1/2013 | Rusin | |
| 2013/0041362 A1 | 2/2013 | Lee et al. | |
| 2013/0041365 A1 | 2/2013 | Rusin et al. | |
| 2013/0053695 A1 | 2/2013 | Brannan | |
| 2013/0067725 A1 | 3/2013 | Behnke, II et al. | |
| 2013/0072920 A1 | 3/2013 | Behnke, II et al. | |
| 2013/0072921 A1 | 3/2013 | Behnke, II et al. | |
| 2013/0072922 A1 | 3/2013 | Behnke, II et al. | |
| 2013/0072923 A1 | 3/2013 | Behnke, II et al. | |
| 2013/0079765 A1 | 3/2013 | Kim et al. | |
| 2013/0085488 A1 | 4/2013 | Brannan et al. | |
| 2013/0103025 A1 | 4/2013 | Brannan | |
| 2013/0103029 A1 | 4/2013 | Brannan | |
| 2013/0110102 A1 | 5/2013 | Prakash et al. | |
| 2013/0123772 A1 | 5/2013 | Bonn et al. | |
| 2013/0126207 A1 | 5/2013 | Rossetto et al. | |
| 2013/0131670 A1 | 5/2013 | Prakash | |

(56) References Cited

U.S. PATENT DOCUMENTS

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1 159 926 A2 | 12/2001 |
| EP | 2221921 A1 | 8/2010 |
| EP | 2361581 A1 | 8/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |
| WO | WO-95/20360 | 8/1995 |
| WO | WO-97/06739 A2 | 2/1997 |
| WO | WO-97/06740 A2 | 2/1997 |
| WO | WO-97/06855 A2 | 2/1997 |
| WO | WO-00/36985 A2 | 6/2000 |
| WO | WO-2006084676 A1 | 8/2006 |
| WO | WO-2010/035831 A1 | 4/2010 |

OTHER PUBLICATIONS

International Search Report from EP Application No. 13003513.2 dated Sep. 12, 2013.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/400,223, filed Feb. 20, 2012, Anthony B. Ross.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/440,440, filed Apr. 30, 2012, Arnold V. Decarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/358,129, filed Jan. 25, 2012, Joseph D. Brannan.
U.S. Appl. No. 13/711,086, filed Dec. 11, 2012, Joseph D. Brannan.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
International Search Report EP11002477 dated Jul. 18, 2011.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPQ, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.

(56) References Cited

OTHER PUBLICATIONS

B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.
Chung et al., "Clinical Experience of Sutureless Closed Hemorrhoidectomy with LigeSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Humphries Jr. et al., "Finite.cndot.Element Codes to Model Electrical Heating and Non.cndot.Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.

(56) References Cited

OTHER PUBLICATIONS

Ni Wei et al., "A Signal Processing Method for the Coriolis Mass Flowmeter Based on a Normalized . . . " Journal of Applied Sciences. cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Roger A. Stern, U.S. Appl. No. 08/136,098, filed Oct. 14, 1993 for Bipolar/Monopolar Endometrial Ablation Device and Method.
Roger A. Stern, U.S. Appl. No. 08/483,742, filed Jun. 7, 1995 for Method and Apparatus for Endometrial Ablation.

\* cited by examiner

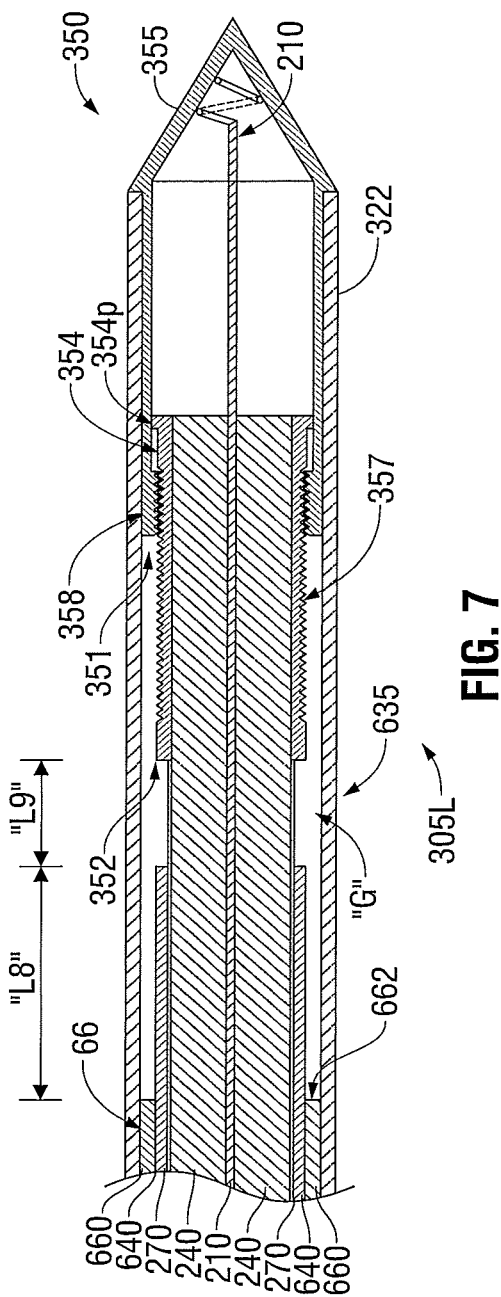
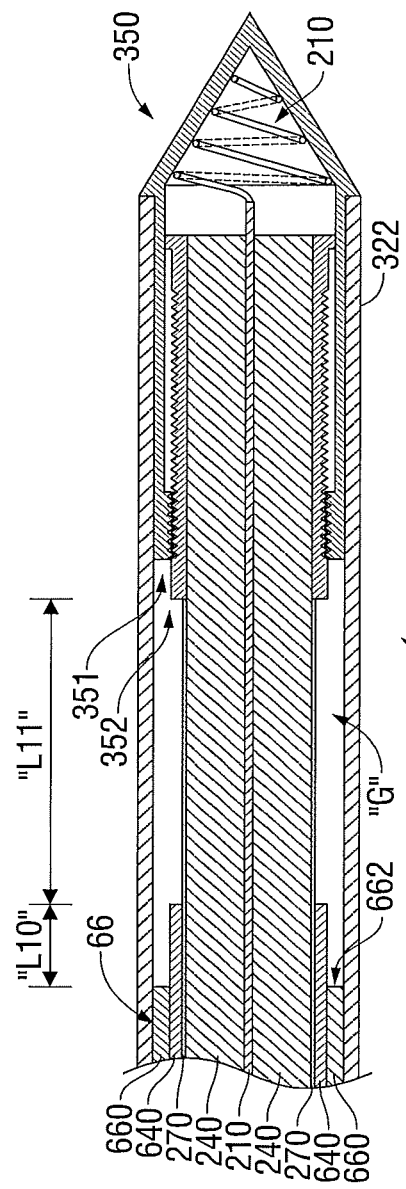
FIG. 7
FIG. 8

ABLATION DEVICES WITH ADJUSTABLE RADIATING SECTION LENGTHS, ELECTROSURGICAL SYSTEMS INCLUDING SAME, AND METHODS OF ADJUSTING ABLATION FIELDS USING SAME

CROSS-REFERENCE TO RELATED APPLICATIONS

The present application is a continuation application, which claims priority to, and the benefit of, U.S. patent application Ser. No. 12/732,508, filed on Mar. 26, 2010, now U.S. Pat. No. 8,409,188, the disclosure of which is herein incorporated by reference in its entirety.

BACKGROUND

1. Technical Field

The present disclosure relates to electrosurgical devices suitable for use in tissue ablation applications and, more particularly, to ablation devices with adjustable radiating section lengths, electrosurgical systems including the same, and methods of adjusting ablation fields using the same.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

A microwave transmission line typically includes a long, thin inner conductor that extends along the longitudinal axis of the transmission line and is surrounded by a dielectric material and is further surrounded by an outer conductor around the dielectric material such that the outer conductor also extends along the transmission line axis. In one variation of an antenna, a waveguiding structure, such as a length of transmission line or coaxial cable, is provided with a plurality of openings through which energy "leaks" or radiates away from the guiding structure. This type of construction is typically referred to as a "leaky coaxial" or "leaky wave" antenna.

During certain procedures, it can be difficult to assess the extent to which the microwave energy will radiate into the surrounding tissue, making it difficult to determine the area or volume of surrounding tissue that will be ablated. Ablation volume is correlated with antenna design, antenna performance, antenna impedance, ablation time and wattage, and tissue characteristics, e.g., tissue impedance. The particular type of tissue ablation procedure may dictate a particular ablation volume in order to achieve a desired surgical outcome. By way of example and without limitation, a spinal ablation procedure may call for a longer, narrower ablation volume, whereas in a prostate ablation procedure a more spherical ablation volume may be required. Treatment of certain tumors may involve probe repositioning during the ablation procedure, such as where the tumor is larger than the probe or has a shape that does not correspond with available probe geometry or radiation pattern.

Ablation procedures may be improved by avoiding inadvertent application of ablative energy to tissue structures, such as large vessels, healthy organs, sensitive neural structures, or vital membrane barriers. Tissue ablation devices capable of influencing ablation volume may enable more precise ablation treatments, which may lead to shorter patient recovery times, fewer complications from undesired tissue damage, and improved patient outcomes.

SUMMARY

The present disclosure relates to an energy applicator for directing energy to tissue including a feedline and a radiating section operably coupled to the feedline, wherein the radiating section has a length. The energy applicator also includes a length adjustment member adapted to allow for selective adjustment of the length of the radiating section.

The present disclosure also relates to an electrosurgical system including a generator and an ablation device. The ablation device includes a feedline and a radiating section having a length, wherein the radiating section is operably coupled to the feedline. The ablation device also includes a radiation field adjustment member adapted to allow for selective adjustment of an ablation field radiated about the radiating section into tissue.

The present disclosure also relates to a method of directing energy to tissue including the initial step of providing an energy applicator. The energy applicator includes a radiating section having a length. A distal portion of the radiating section includes an inner conductor and a length adjustment member electrically coupled to the inner conductor. The length adjustment member is adapted to allow for dimensional adjustment of the radiating section. The method also includes the steps of positioning the energy applicator in tissue, and transmitting energy from an energy source through the radiating section to generate an ablation field radiating about at least a portion of the energy applicator into tissue.

BRIEF DESCRIPTION OF THE DRAWINGS

Objects and features of the presently disclosed ablation devices with adjustable radiating section lengths, electrosurgical systems including the same, and methods of adjusting ablation fields using the same will become apparent to those of ordinary skill in the art when descriptions of various embodiments thereof are read with reference to the accompanying drawings, of which:

FIG. 7 shows a partial, cross-sectional view of the ablation device of FIG. 6 shown with the length adjustment member adjusted to elongate the distal radiating section and the gap adjustment member adjusted to shorten the distance across the gap at the feed point according to an embodiment of the present disclosure;

FIG. 8 shows a partial, cross-sectional view of the ablation device of FIG. 6 shown with the length adjustment member adjusted to shorten the distal radiating section and the gap adjustment member adjusted to lengthen the distance across the gap at the feed point according to an embodiment of the present disclosure;

DETAILED DESCRIPTION

Figure 1:
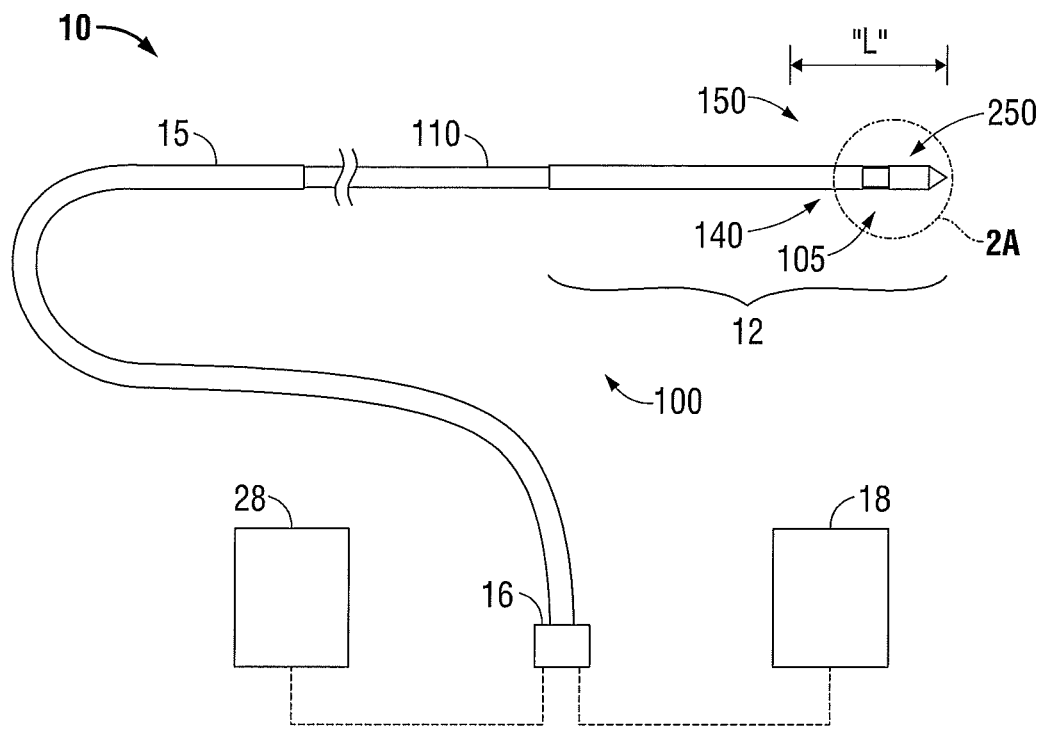
FIG. 1 is a schematic diagram of an ablation system including an ablation device with adjustable radiating section lengths according to an embodiment of the present disclosure.

Hereinafter, embodiments of the presently disclosed ablation devices with adjustable radiating section lengths, electrosurgical systems including the same, and methods of adjusting ablation fields using the same are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the ablation device, or component thereof, closer to the user and the term "distal" refers to that portion of the ablation device, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second). As it is used in this description, "ablation procedure" generally refers to any ablation procedure, such as microwave ablation, radio frequency (RF) ablation or microwave ablation assisted resection. As it is used in this description, "energy applicator" generally refers to any device that can be used to transfer energy from a power generating source, such as a microwave or RF electrosurgical generator, to tissue. As it is used in this description, "energy applicator array" generally refers to one or more energy applicators. As it is used in this description, "transmission line" generally refers to any transmission medium that can be used for the propagation of signals from one point to another.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

Various embodiments of the present disclosure provide ablation devices with adjustable radiating section lengths for treating tissue and methods of directing electromagnetic radiation to tissue. Embodiments may be implemented using electromagnetic radiation at microwave frequencies or at other frequencies. An electrosurgical system including an ablation device with adjustable radiating section lengths, according to various embodiments, is designed and configured to operate between about 300 MHz and about 10 GHz.

The ablation field radiated about an energy applicator into tissue is affected by many factors including the antenna radiating section length, e.g., in relationship to microwave frequency. The ablation field radiated into tissue may also be affected by the gap distance of the feed point, e.g., in the dipole antenna assembly. Ablation devices according to embodiments of the present disclosure may include a length adjustment member (e.g., 350 shown in FIG. 3) adapted to allow for dimensional adjustment of a radiating section. In some embodiments, the presently disclosed length adjustment members may be configured to effect changes in the length of a distal radiating section. Embodiments of ablation devices in accordance with the present disclosure may additionally, or alternatively, include a gap adjustment member (e.g., 640 shown in FIG. 6) adapted to allow for selective adjustment of the gap distance of the feed point.

Various embodiments of the presently disclosed ablation device with adjustable radiating section lengths are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

FIG. 1 shows an electrosurgical system 10 according to an embodiment of the present disclosure that includes an energy applicator (also referred to herein as an ablation device) or probe 100. An embodiment of an energy applicator suitable for use in tissue ablation applications, such as the probe 100 of FIG. 1, in accordance with the present disclosure, is shown in more detail in FIGS. 2A and 2B. It will be understood, however, that other probe embodiments (e.g., 301, 601 and 901 shown in FIGS. 3, 6 and 11, respectively) may also be used.

Figure 2A:
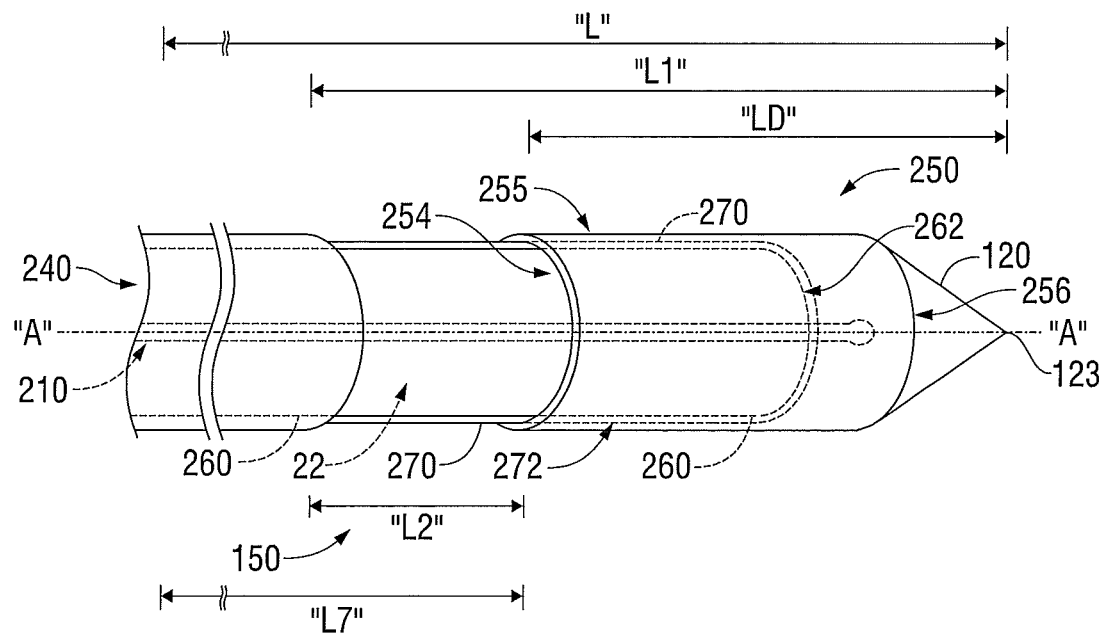
FIG. 2A is an enlarged view of the indicated area of detail of FIG. 1 showing an embodiment of a length adjustment member in accordance with the present disclosure.

Probe 100 generally includes an antenna assembly 12 having a radiating portion 150 connected by a feedline 110 (or shaft) via a transmission line 15 to a connector 16, which may further operably connect the probe 100 to an electrosurgical power generating source, e.g., a microwave or RF electrosurgical generator, or a generator assembly 28. Probe 100 according to various embodiments includes a radiating section 150 having a length (e.g., "L" shown in FIGS. 1 and 2A). As shown in FIGS. 1 and 2A, the probe 100 may include a length adjustment member 250 configured to allow selective adjustment of the length of the radiating section 150. An adjustment of the length of the radiating section 150 by adjusting the length adjustment member 250, which is described in more detail later in this disclosure, may be made automatically or manually by the user.

Probe 100 may include a proximal radiating section 140 and a distal radiating section 105, which are described later in this disclosure. In some embodiments, the radiating section 150 has a length "L" (shown in FIGS. 1 and 2A), and the distal radiating section 105 has a length "LD" (shown in FIG. 2A) and the proximal radiating section 140 has a length "L7" (shown in FIG. 2A), such that L=LD+L7. The shape and size of the antenna assembly 12 and the radiating section 150 may be varied from the configuration depicted in FIG. 1 (e.g., radiating section 150 may have a length "L1", as shown in FIG. 2A).

Feedline 110 may be formed from a suitable flexible, semi-rigid or rigid microwave conductive cable, and may connect directly to an electrosurgical power generating source 28. Alternatively, the feedline 110 may electrically connect the antenna assembly 12 via the transmission line 15 to the generator 28. Feedline 110 may have a variable length from a proximal end of the antenna assembly 12 to a distal end of transmission line 15 ranging from a length of about one inch to about twelve inches. Feedline 110 may be formed of suitable electrically-conductive materials, e.g., copper, gold, silver or other conductive metals or metal alloys having similar conductivity values. Feedline 110 may be made of stainless steel, which generally offers the strength required to puncture tissue and/or skin. Conductive materials used to form the feedline 110 may be plated with other materials, e.g., other conductive materials, such as gold or silver, to improve their properties, e.g., to improve conductivity, or decrease energy loss, etc. In some embodiments, the feedline 110 includes stainless steel, and to improve the conductivity thereof, the stainless steel may be coated with a layer of a conductive material such as copper or gold. Feedline 110 may include an inner conductor, a dielectric material coaxially surrounding the inner conductor, and an outer conductor coaxially surrounding the dielectric material. Antenna assembly 12 may be formed from a portion of the inner conductor (e.g., 210 shown in FIG. 2A) that extends distal of the distal-most end of the outer conductor 260. Feedline 110 may be cooled by fluid, e.g., saline or water, to improve power handling, and may include a stainless steel catheter.

In some embodiments, the power generating source 28 is configured to provide microwave energy at an operational frequency from about 300 MHz to about 2500 MHz. In other embodiments, the power generating source 28 is configured to provide microwave energy at an operational frequency from about 300 MHz to about 10 GHz. Power generating source 28 may be configured to provide various frequencies of electromagnetic energy. Transmission line 15 may additionally, or alternatively, provide a conduit (not shown) configured to provide coolant fluid from a coolant source 18 to the probe 100.

Antenna assembly 12 generally includes an inner conductor 210, an outer conductor 260, and may include a dielectric material 240 separating the inner conductor 210 and the outer conductor 260. Length adjustment member 250 according to various embodiments is electrically coupled to the inner conductor 210 by any suitable manner of electrical connection, e.g., soldering, welding, or laser welding. In some embodiments, the inner conductor 210 is formed from a first electrically-conductive material (e.g., stainless steel) and the outer conductor 260 is formed from a second electrically-conductive material (e.g., copper). In some embodiments, the outer conductor 260 coaxially surrounds the inner conductor 210 along at least a portion of the antenna assembly 12. Inner conductor 210 and the outer conductor 260 may be formed from any suitable electrically-conductive material.

According to embodiments of the present disclosure, the distal end of the outer conductor 260 may be spaced apart by a gap (e.g., "G" shown in FIGS. 6 and 8) from the proximal end of the distal radiating section to define a feed point (e.g., 635 shown in FIG. 6) therebetween. Electrical chokes or non-electrical (fluid) chokes may be used to contain returning currents to the distal end of the antenna assembly 12, e.g., to improve the energy focus of an antenna assembly 12. Generally, the choke may be disposed on the antenna assembly 12 proximally of or as a part of the radiating section.

The dielectric material 240 may be formed from any suitable dielectric material, including, but not limited to, ceramics, water, mica, polyethylene, polyethylene terephthalate, polyimide, polytetrafluoroethylene (PTFE) (e.g., TEFLON®, manufactured by E. I. du Pont de Nemours and Company of Wilmington, Del., United States), glass, or metal oxides. Antenna assembly 12 may be provided with a second dielectric material (e.g., 270 shown in FIG. 2A) surrounding the outer conductor 260, or portions thereof. In some embodiments, the second dielectric material is formed from a material with a dielectric constant different than the dielectric constant of the dielectric material 240.

Located at the distal end of the antenna assembly 12 is an end cap or tapered portion 120, which may terminate in a sharp tip 123 to allow for insertion into tissue with minimal resistance. The end cap or tapered portion 120 may include other shapes, such as, for example, a tip 123 that is rounded, flat, square, hexagonal, or cylindroconical. Tip 123 may be coated with a non-stick material, such as polytetrafluoroethylene (a.k.a. PTFE or TEFLON®, manufactured by the E. I. du Pont de Nemours and Company of Wilmington, Del., United States), polyethylene tephthalate (PET), or the like.

In some variations, the antenna assembly 12 includes a proximal radiating section 140 and a distal radiating section 105. In some embodiments, a junction member (not shown), which is generally made of a dielectric material couples the proximal radiating section 140 and the distal radiating section 105. In some embodiments, the distal and proximal radiating sections 105, 140 align at the junction member and are also supported by the inner conductor that extends at least partially through the distal radiating section 105. The junction member according to various embodiments may be formed from any suitable elastomeric or ceramic dielectric material by any suitable process. In some embodiments, the junction member is formed by overmolding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VESPEL®, manufactured by E. du Pont de Nemours and Company of Wilmington, Del., United States). The junction member may be formed using any suitable overmolding compound by any suitable process, and may include use of a ceramic substrate. Examples of junction member embodiments are disclosed in commonly assigned U.S. patent application Ser. No. 12/701,030 filed on Feb. 5, 2010, entitled "ELECTROSURGICAL DEVICES WITH CHOKE SHORTED TO BIOLOGICAL TISSUE".

In some embodiments, the antenna assembly 12 may be provided with a coolant chamber (not shown). Additionally, the junction member may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401, 268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS".

In some embodiments, the antenna assembly 12 may be provided with an outer jacket (not shown) disposed about the distal radiating section 105, or portions thereof, the proximal radiating section 140, or portions thereof, and/or the feedline 110, or portions thereof. The outer jacket may be formed of any suitable material, such as, for example, polymeric or ceramic materials. The outer jacket may be applied by any suitable method, such as, for example, heat shrinking, overmolding, coating, spraying dipping, powder coating, baking and/or film deposition.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or atop tissue, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may be used to provide ablations in short procedure times, e.g., a few seconds to minutes, to destroy cancerous cells in the target tissue region.

A plurality of probes 100 may be placed in variously arranged configurations to substantially simultaneously ablate a target tissue region, making faster procedures possible. Multiple probes 100 can be used to synergistically create a large ablation volume or to ablate separate sites simultaneously. Tissue ablation size and geometry is influenced by a variety of factors, such as the energy applicator design, number of energy applicators used simultaneously, ablation time and wattage, and tissue characteristics.

In operation, microwave energy having a wavelength, lambda ($\lambda$), is transmitted through the antenna assembly 12, e.g., along the distal radiating section 105, and radiated into the surrounding medium, e.g., tissue. The length of the antenna for efficient radiation may be dependent on the effective wavelength, $\lambda_{eff}$, which is dependent upon the dielectric properties of the medium being radiated into. Antenna assembly 12 through which microwave energy is transmitted at a wavelength, $\lambda$, may have differing effective wavelengths, $\lambda_{eff}$, depending upon the surrounding medium, e.g., liver tissue as opposed to breast tissue.

As shown in FIGS. 1 and 2A, the antenna assembly 12 according to embodiments of the present disclosure includes a length adjustment member 250 adapted to allow for dimensional adjustment of the radiating section 150. Length adjustment member 250 according to various embodiments includes a sleeve portion 255 including a proximal end 254 and a distal end 256. Sleeve portion 255 may have a substantially cylindrical or tubular shape and may be formed from stainless steel. Tapered portion 120 may be disposed adjacent to the distal end 256 of the sleeve portion 255. Tapered portion 120 may be formed of a first electrically-conductive material and the sleeve portion 255 may be formed of a second electrically-conductive material different than the first electrically-conductive material. Tapered portion 120 may be formed of a material with high thermal conductivity. The shape and size of the sleeve portion 255 and the tapered portion 120 may be varied from the configuration depicted in FIGS. 1 and 2A.

In some embodiments, the antenna assembly 12 includes an insulator sleeve 270 disposed around at least a portion of the outer conductor 260. As shown in FIG. 2A, the sleeve portion 255 may be disposed around at least a distal portion 272 of the insulator sleeve 270. In some embodiments, the insulator sleeve 270 and the sleeve portion 255 may be substantially concentric to a longitudinal axis (e.g., "A-A" shown in FIG. 2A) of the inner conductor 210. Insulator sleeve 270 may extend distally beyond the distal end 256 of the outer conductor 260, e.g., to enhance slideability and/or repositionability of the sleeve portion 255. The shape and size of the insulator sleeve 270 may be varied from the configuration depicted in FIGS. 2A and 2B.

Insulator sleeve 270 may be formed of any suitable non-conductive insulator, e.g., a TEFLON® sleeve. In some embodiments, the insulator sleeve 270 is a lubricous sleeve. Insulator sleeve 270 may be applied by any suitable manner, including, but not limited to, by applying a polymeric coating, and/or by positioning a heat-shrinkable tube (e.g., polyolefin) and raising the temperature thereof to conform the heat shrink tubing to the outer conductor 260. Insulator sleeve 270 may be selected based on materials properties, e.g., density and lubricity, to allow for sliding of the sleeve portion 255, or portions thereof, over the insulator sleeve 270. Insulator sleeve 270 may additionally, or alternatively, be selected to prevent damage and/or minimize wear to the insulator sleeve 270 and/or the sleeve portion 255. Insulator sleeve 270 may be formed of a lubricous polymeric material, such as a high-density polyolefin (e.g., polyethylene), polytetrafluoroethylene (a.k.a. PTFE or TEFLON®, manufactured by E. I. du Pont de Nemours and Company of Wilmington, Del., United States), or polyurethane. Insulator sleeve 270 may be formed by heat-shrinkage, extrusion, molding, dip coating, or other suitable process. In some embodiments, the insulator sleeve 270 may include a surface coating formed of highly hydrophilic, low-friction polymer, such as polyvinylpyrrolidone, polyethyleneoxide, polyhydroxyethylmethacrylate, or copolymers thereof. Insulator sleeve 270 may be formed from a material with a dielectric constant that is higher than the dielectric constant of the dielectric material 240, e.g., to maximize energy radiated into the surrounding medium, e.g., tissue. Insulator sleeve 270 may be formed of materials that can be made hydrophilic for a predetermined period of time during the procedure, e.g., by contact with water and/or other bodily fluids such as blood.

Length adjustment member 250 according to various embodiments may have a first position (e.g., a proximal-most position) corresponding to a radiating section 150 having a relatively short length "L1" (shown in FIG. 2A), a second position (e.g., a distal-most position), corresponding to a radiating section 150L having a relatively long length "L3" (shown in FIG. 2B), and a plurality of intermediate positions corresponding to radiating sections of intermediate lengths. In some embodiments, the distance "L1" is about 1 cm, and the distance "L3" may be about 5 cm.

Figure 2B:
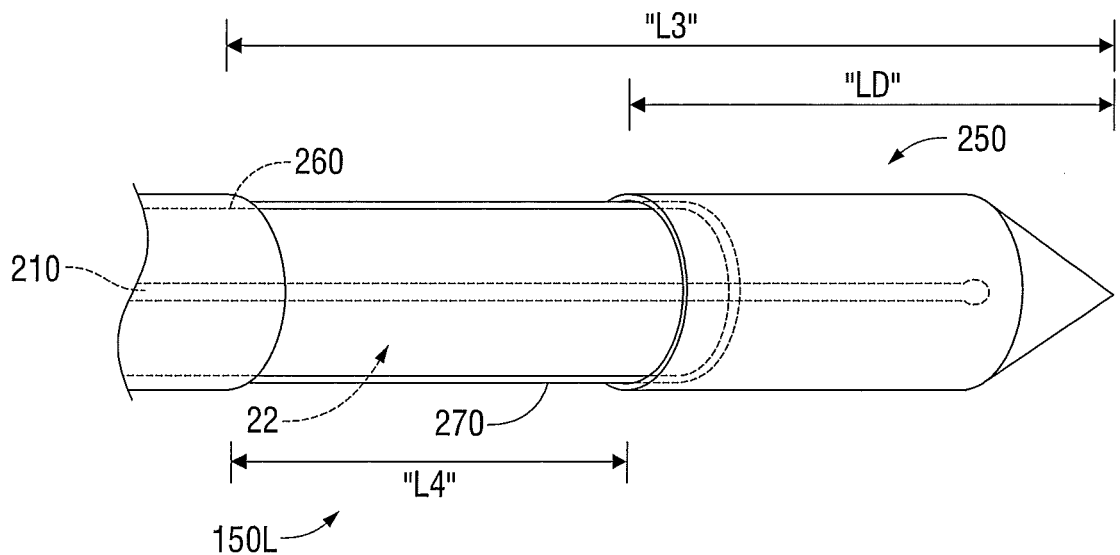
FIG. 2B is a partial, perspective view of the ablation device of FIG. 1 shown with the length adjustment member adjusted to elongate the distal radiating section according to an embodiment of the present disclosure.

In some embodiments, when the length adjustment member 250 is positioned in a first position, e.g., corresponding to a radiating section 150 having a relatively short length "L1" (shown in FIG. 2A), the distal portion 250 of the antenna radiating section extends by a fixed length "LD" distally beyond the proximal radiating section 22, which is formed by the exposed portion of the underlapping outer conductor, and has a length "L2", such that L1=LD+L2. As shown in FIG. 2B, when the length adjustment member 250 is placed in a second position, e.g., corresponding to a radiating section 150L having a relatively long length "L3", the distal portion 250 of radiating section still extends by the fixed length "LD" distally beyond the proximal radiating section 22, which has a length "L4", such that L3=LD+L4. The distances "L2" and "L4" may be any suitable length and may be measured in fractions of a wavelength. In some embodiments, the distance "L2" is about 1 mm, and the distance "L4" may be about 4 cm.

Selective adjustment of the length adjustment member 250, according to various embodiments, allows a portion of the underlapping outer conductor extending proximally to the length adjustment member 250 to be varied in length, which may enhance microwave performance of the probe 100 and/or provide a desired ablation volume and shape. For example, a radiating section (e.g., 150 shown in FIG. 2A) having a relatively short length, e.g., "L1", for use to generate local temperatures that result in a small ablation volume may be suitable for treatment of a small tumor, e.g., using a frequency of 915 MHz. In a resection procedure, where the surgeon may want to extend the distal radiating section as far distally as possible, a radiating section (e.g., 150L shown in FIG. 2B) having a relatively long length, e.g., "L3", may be fashioned by using the length adjustment member 250 to adjust the length of the proximal radiating section. During a procedure, selective adjustment of the length of the proximal radiating section using the length adjustment member 250 may be carried out any number of times, e.g., to enhance microwave performance of the probe 100 and/or provide a desired ablation pattern.

Probe 100 may be configured to operate with a directional radiation pattern. Probe 100 may be rotatable about a longitudinal axis "A-A" (shown in FIG. 2A) such that the directional radiation pattern rotates therewith. Examples of antenna assemblies rotatable about axis "A-A" such that any elongated radiation lobes rotates therewith are disclosed in commonly assigned U.S. patent application Ser. No. 12/197,405 filed on Aug. 25, 2008, entitled "MICROWAVE ANTENNA ASSEMBLY HAVING A DIELECTRIC BODY PORTION WITH RADIAL PARTITIONS OF DIELECTRIC MATERIAL".

Figure 3:
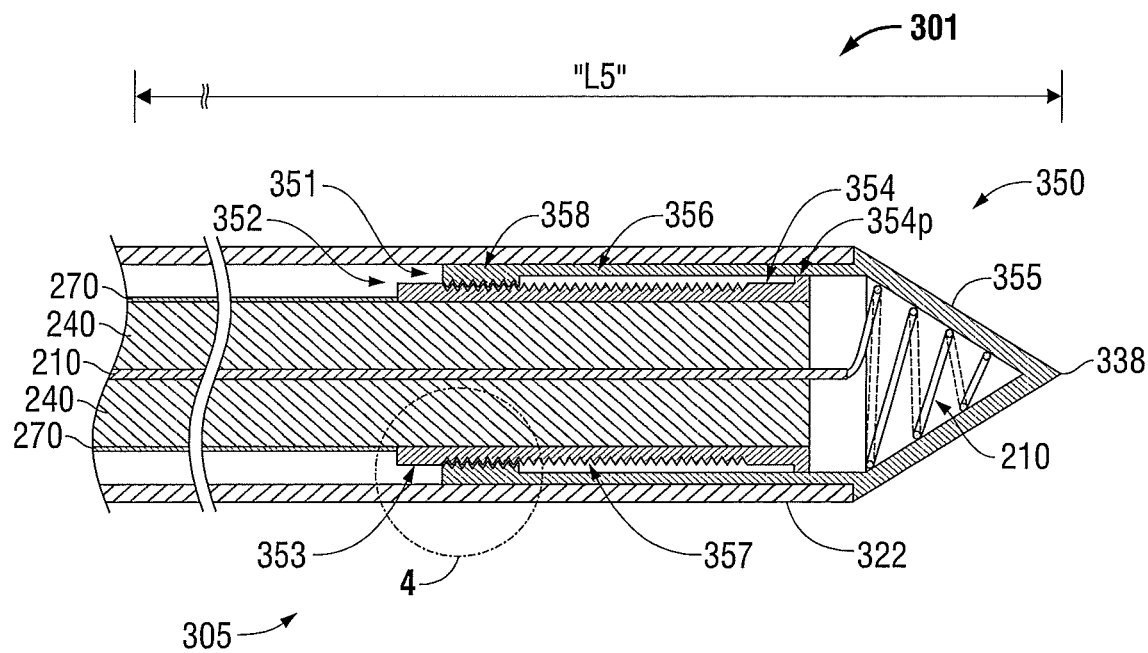
FIG. 3 is a partial, cross-sectional view of an ablation device shown with another embodiment of a length adjustment member in accordance with the present disclosure.

FIG. 3 shows a portion of an ablation device 301 according to an embodiment of the present disclosure that includes an inner conductor 210, a dielectric material 240 disposed coaxially around the inner conductor 210, and a length adjustment member 350 adapted to allow for dimensional adjustment of a distal radiating section 305. As shown in FIG. 3, the inner conductor 210 may extend distally beyond the dielectric material 240. Inner conductor 210 may be formed from a yieldable or flexible material.

Figure 5:
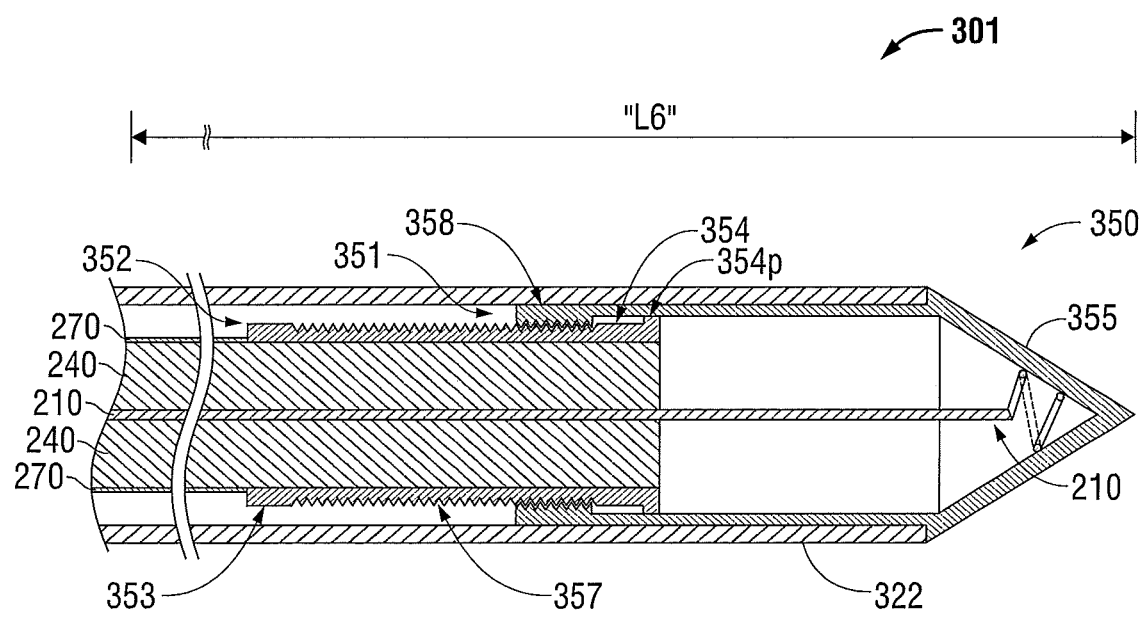
FIG. 5 is a partial, cross-sectional view of the ablation device of FIG. 3 shown with the length adjustment member adjusted to elongate the distal radiating section according to an embodiment of the present disclosure.

As cooperatively shown in FIGS. 3 and 5, the length adjustment member 350 may have a first position (e.g., a proximal-most position) corresponding to a distal radiating section 305 having a relatively short length "L5", a second position (e.g., a distal-most position), corresponding to a distal radiating section 305L having a relatively long length "L6", and a plurality of intermediate positions corresponding to distal radiating sections of intermediate lengths. In some embodiments, the distance "L5" is about 1 cm, and the distance "L6" may be about 5 cm. In some embodiments, the length adjustment member 350 includes a tapered end portion (e.g., 355 shown in FIG. 3) that terminates in a sharp tip (e.g., 338 shown in FIG. 3) at the distal end of the distal radiating section. The tapered end portion allows for insertion of the probe into tissue with minimal resistance. The tapered end portion may include other shapes, such as, for example, a tip that is rounded, flat, square, hexagonal, or cylindroconical.

Figure 4:
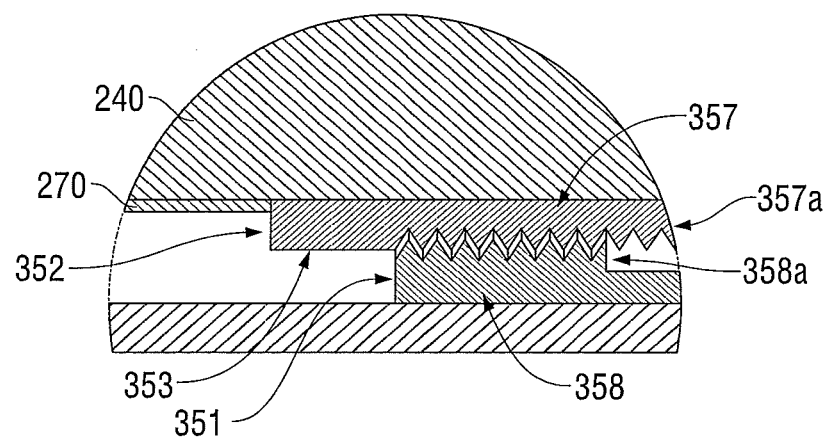
FIG. 4 is an enlarged view of the indicated area of detail of FIG. 3 according to an embodiment of the present disclosure.

Length adjustment member 350 according to various embodiments includes an inner sleeve 352 and an outer sleeve 351 disposed around at least a portion of the inner sleeve 352. Outer sleeve 351 and the inner sleeve 352 may be of different sizes, diameters and thickness. As shown in FIGS. 3 and 4, the inner sleeve 352 may include a proximal end portion 353, a distal end portion 354 and a threaded middle portion 357 disposed between the proximal and distal end portions 353, 354, and the outer sleeve 351 may include a tapered end portion 355, a middle portion 356, and a threaded end portion 358 engaged with the threaded middle portion 357 of the inner sleeve 352. Outer sleeve 351 and the inner sleeve 352 may be formed of any suitable electrically-conductive material, e.g., metal such as stainless steel, titanium, etc. In some embodiments, the inner sleeve 352 may be formed of any rigid dielectric material. The shape and size of the outer sleeve 351 and the inner sleeve 352 may be varied from the configuration depicted in FIGS. 3 through 5.

When the length adjustment member 350 is positioned in a first position (e.g., a proximal-most position), a second position (e.g., a distal-most position) or an intermediate position between the first and second positions, a plurality of threads (e.g., 358a shown in FIG. 4) of the threaded end portion 358 engage with a plurality of threads (e.g., 357a shown in FIG. 4) of the threaded middle portion 357. As shown in FIGS. 3 and 4, when the outer sleeve 351 is placed in a proximal-most position, the threaded end portion 358 engages with a proximal portion of the threaded middle portion 357 disposed closest to the proximal end portion 353 of the inner sleeve 352. As shown in FIG. 5, when the outer sleeve 351 is placed in a distal-most position, the threaded end portion 358 engages with a distal portion of the threaded middle portion 357 disposed closest to the distal end portion 354 of the inner sleeve 352.

In some embodiments, the distal end portion 354 of the inner sleeve 352 may include a mechanical interface configured to engage the middle portion 356 of the outer sleeve 351. As shown in FIG. 3, the distal end portion 354 of the inner sleeve 352 may include a protrusion 354p configured to slideably engage an inner surface of the middle portion 356 of the outer sleeve 351, e.g., to enhance structural integrity of the length adjustment member 350 and/or maintain proper alignment of the threads 357a, 358a. The shape and size of the protrusion 354p may be varied from the configuration depicted in FIGS. 3 and 5. In some embodiments, friction on the outer sleeve 351 may be reduced by minimizing the surface area of the protrusion 354p that contacts the inner surface of the middle portion 356 of the outer sleeve 351.

Ablation device 301, or portions thereof, may be provided with a flexible, outer coating or jacket material 322. In some embodiments, the jacket material 322 may be disposed around the length adjustment member 350, or portions thereof. Any material having suitable material properties, e.g., elasticity, may be used for the jacket material 322, e.g., a stretchable polymer heat shrink.

In some embodiments, the length adjustment member 350 can be made longer or shorter in length by spinning the inner sleeve 352 and the outer sleeve 351 in relationship to one another. The elastic, resilience or yieldable properties of the inner conductor 210 may allow a coiled portion of the inner conductor 210 to wind or unwind, e.g., as the length adjustment member 350 is adjusted.

Ablation device 301 according various embodiments may be adapted to allow for selective adjustment of the length of the distal radiating section using the length adjustment member 350 during an automatic adjustment process, e.g., to adjust the ablation field radiated into tissue. Ablation device 301 may be rotatable about a longitudinal axis such that a directional radiation pattern rotates therewith.

Figure 6:
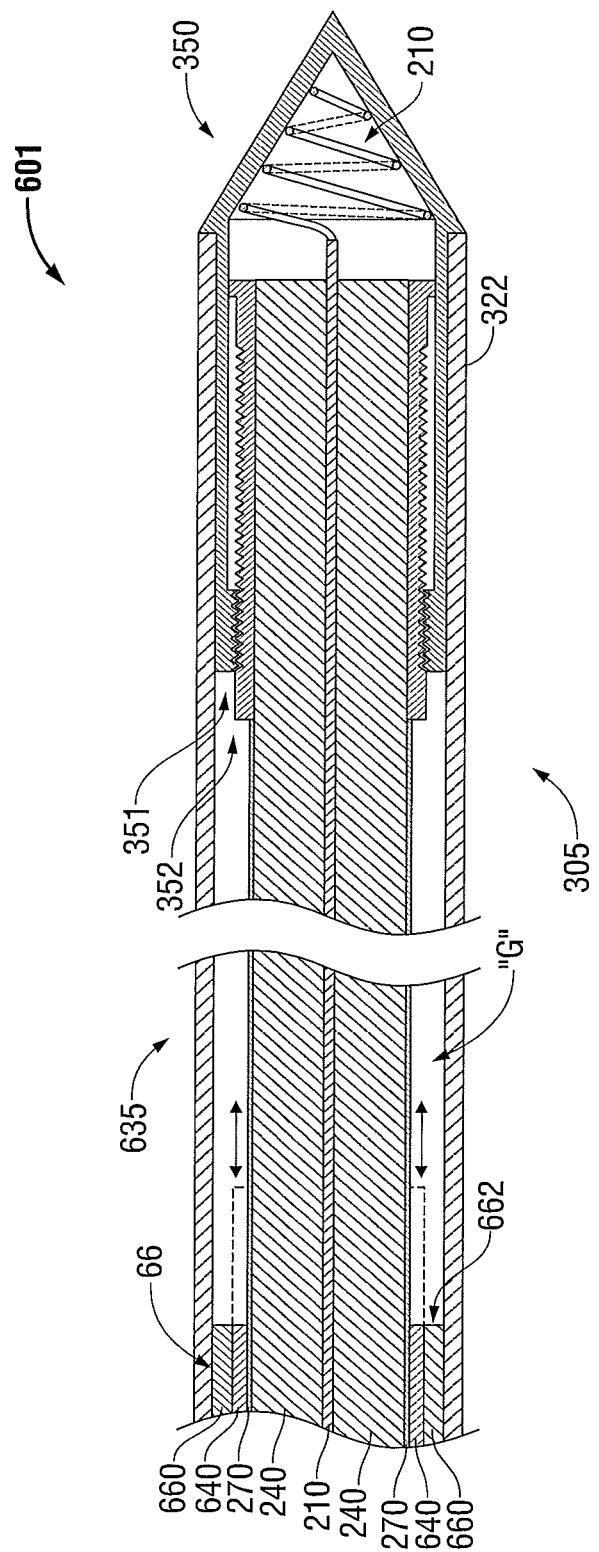
FIG. 6 is a partial, cross-sectional view of the ablation device of FIG. 3 shown with a gap adjustment member disposed proximal to the length adjustment member according to an embodiment of the present disclosure.

FIG. 6 shows a portion of an ablation device 601 according to an embodiment of the present disclosure that is similar to the portion of the ablation device 301 of FIG. 3, except for a gap adjustment member 640, which is described later in this disclosure, disposed proximal to the length adjustment member 350. Ablation device 601 includes an inner conductor 210, a dielectric material 240 disposed coaxially around the inner conductor 210, and an outer conductor 260, and may include an insulator sleeve 270 disposed around the dielectric material 240, or portions thereof. The inner conductor 210, the dielectric material 240, and the insulator sleeve 270 shown in FIG. 6 are similar to the elements designated with like reference numerals in FIGS. 3 through 5, and further description thereof is omitted in the interests of brevity.

Embodiments of the ablation device 601 may include the length adjustment member 350 shown in FIGS. 3 through 5. Length adjustment member 350 may be adjustable to a distal-most position, a proximal-most position, and a plurality of intermediate positions. As shown in FIG. 7, when the outer sleeve 351 is placed in a distal-most position, the threaded end portion 358 engages with a distal portion of the threaded middle portion 357 disposed closest to the distal end portion 354 of the inner sleeve 352, corresponding to a distal radiating section 305L having a relatively long length (e.g., "L6" shown in FIG. 5). As shown in FIG. 8, when the outer sleeve 351 is placed in a proximal-most position, the threaded end portion 358 engages with a proximal portion of the threaded middle portion 357 disposed closest to the proximal end portion 353 of the inner sleeve 352, corresponding to a distal radiating section 305 having a relatively short length (e.g., "L5" shown in FIG. 3). The shape and size of the length adjustment member 350 may be varied from the configurations depicted in FIG. 6 and FIGS. 7 and 8.

Outer conductor 660 may be formed from any suitable electrically-conductive material, e.g., metal such as copper, aluminum, stainless steel, or other suitable metal. As shown in FIG. 6, the distal end 662 of the outer conductor 660 may be spaced apart by a gap "G" from the proximal end of the distal radiating section 305 to define a feed point 635 therebetween.

Gap adjustment member 640 according to various embodiments is adapted to allow for selective adjustment of the gap distance of the feed point 635, e.g., to enhance microwave performance of the probe 100 and/or provide a desired ablation pattern. For example, when a smaller ablation with a more spherical or donut shape ablation is desired, the ablation device 601 may be adjusted to its most compact length with a reduced radiating section tuning point, e.g., one-quarter wavelength in tissue. When an ablation device is needed to produce longer, narrower ablations (e.g., in resection procedures) the gap and the distal radiating section length may be expanded to fuller lengths by adjusting the gap adjustment member 640 and the length adjustment member 350. In some embodiments, the gap adjustment member 640 and/or the length adjustment member 350 may be adjusted manually by the user and/or automatically, e.g., by the presently disclosed electrosurgical system 1000 (shown in FIG. 9). Gap adjustment member 640 according to embodiments may take a variety of forms, e.g., moveable sleeves and/or moveable arms, with or without lubrication.

Gap adjustment member 640 may be formed of any suitable electrically-conductive material, e.g., metal such as copper, stainless steel, titanium, etc. As shown in FIG. 6, the gap adjustment member 640 may be coaxially disposed around an insulator sleeve 270 disposed around the dielectric material

240. Gap adjustment member 640 may be configured to move, e.g., slide, longitudinally along the insulator sleeve 270 in a distal-to-proximal direction, e.g., to shorten the gap distance of the feed point 635, and a proximal-to-distal direction, e.g., to lengthen the gap distance of the feed point 635 (as shown by the double-arrowhead lines in FIG. 6). In some embodiments, the gap adjustment member 640 may be coaxially disposed around the dielectric material 240, wherein the dielectric material 240 has material properties, e.g., density, to allow for sliding of the gap adjustment member 640 along the outer surface of the first dielectric material without damage to the dielectric material 240 and/or the gap adjustment member 640. Outer conductor 660 is electrically coupled to the gap adjustment member 640. In some embodiments, the distal end portion 66 of the outer conductor 260 is coaxially disposed around at least a portion of the gap adjustment member 640. The outer surface of the gap adjustment member 640, or portions thereof, may be coated with a suitable lubricious substance (not shown) to aid in the movement of the gap adjustment member 640. The lubricious substance may be an electrically-conductive substance. The shape and size of the gap adjustment member 640 may be varied from the configuration depicted in FIG. 6.

An outer jacket (not shown) may be provided to the probe 601, or portions thereof, e.g., disposed proximal to the distal radiating section. In some embodiments, the outer jacket may be made of an insulating material, such as, for example, a polyimide or similar dielectric material. The outer jacket may be a water-cooled catheter formed of a material having low electrical conductivity. During use, coolant may circulate through the outer jacket, which may help control the temperature of the probe 601, and may provide dielectric loading within the radiating section. The outer surface of the outer jacket may be coated with a suitable lubricious substance, such as TEFLON®, to aid in the movement of the outer jacket in or through tissue as well as to aid in preventing tissue from sticking thereto.

Ablation device 601 may include an indicia alignment mark (not shown) such as a colored strip or the like (e.g., to provide a visual cue to the surgeon to allow orientation of the direction of flow of the energy to coincide with the indicia alignment mark) and/or indicia graduation marks (not shown) for insertion depth reference. Examples of indicia alignment mark and the indicia graduation mark embodiments are disclosed in commonly assigned U.S. patent application Ser. No. 12/476,960 filed on Jun. 2, 2009, entitled "ELECTROSURGICAL DEVICES WITH DIRECTIONAL RADIATION PATTERN".

Ablation device 601 according to various embodiments is adapted to allow the surgeon to adjust the length of the distal radiating section and the gap distance of the feed point to any suitable configuration, e.g., to adjust the ablation field and/or achieve a desired surgical outcome. For example, as shown in FIG. 7, the length adjustment member 350 may be adjusted to provide an elongated distal radiating section 305L, and the gap adjustment member 640 according to an embodiment of the present disclosure may be distally extended from the distal end 662 of the outer conductor 660 by a length "L8" to shorten the gap distance of the feed point to a length "L9", which may correspond to a relatively small gap distance. In some embodiments, the distance "L8" is about 5 mm, and the distance "L9" may be about 0.5 mm. As shown in FIG. 8, the length adjustment member 350 may be adjusted to provide a distal radiating section 305 having a relatively short length, and the gap adjustment member 640 according to an embodiment of the present disclosure may be adjusted by a length "L10" to provide a gap distance of a length "L11", e.g., to adjust the ablation field. In some embodiments, the distance "L10" is about 0.5 mm, and the distance "L11" may be about 10 mm.

Figure 9:
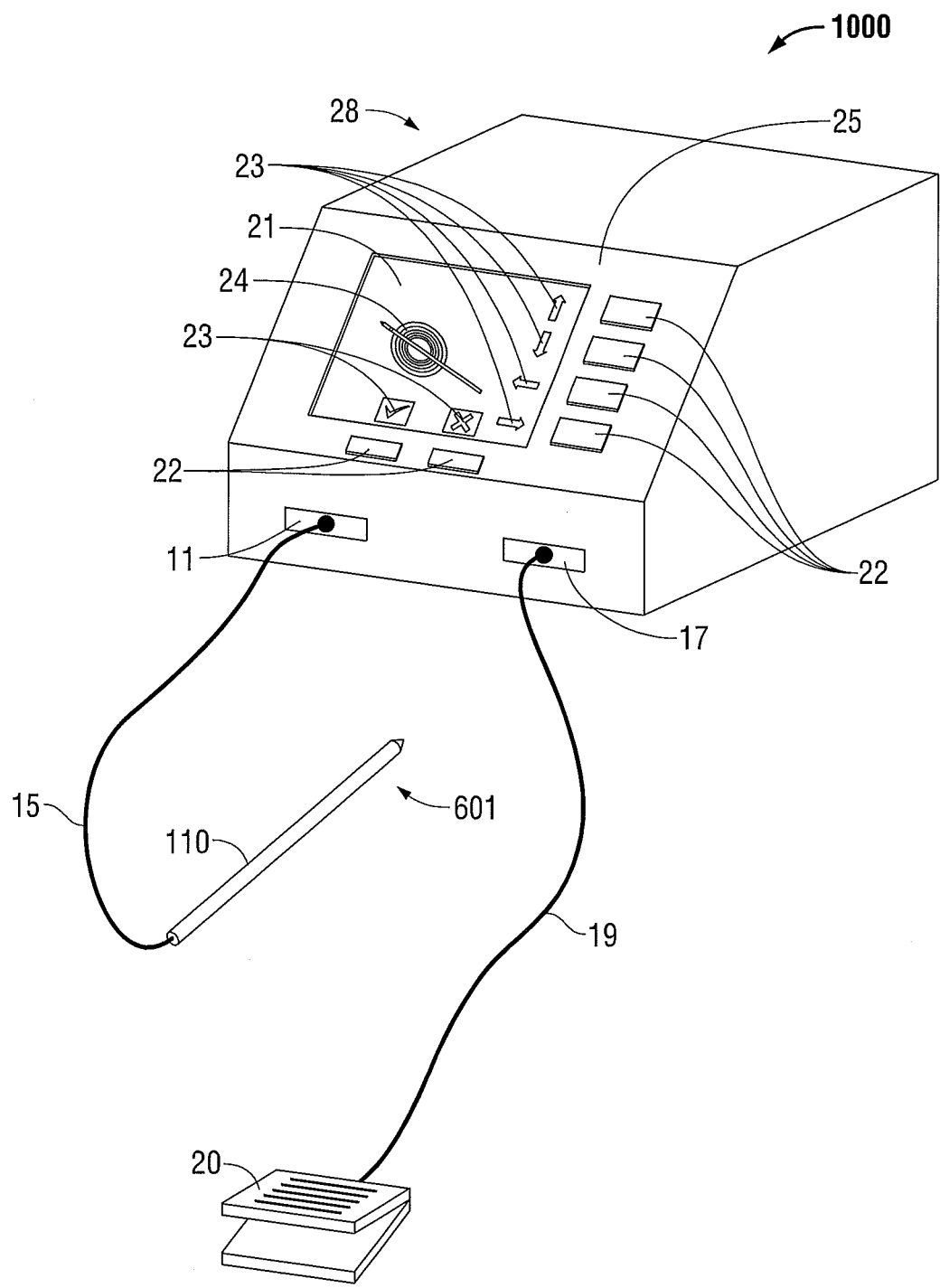
FIG. 9 shows a diagram of a microwave ablation system that includes a user interface for displaying and controlling ablation patterns in accordance with the present disclosure.

FIG. 9 schematically illustrates an electrosurgical system 1000 according to an embodiment of the present disclosure including the ablation device or probe 601. It will be understood, however, that other probe embodiments (e.g., 301 and 901 shown in FIGS. 3 and 9, respectively) may also be used. Electrosurgical system 1000 includes an actuator 20 operably coupled to an embodiment of the generator assembly 28 of the electrosurgical system 10 of FIG. 1. Actuator 20 may be a footswitch operably coupled by a cable 19 via connector 17 to the generator assembly 28, a handswitch, a bite-activated switch, or any other suitable actuator. Cable 19 may include one or more electrical conductors for conveying an actuation signal from the actuator 20 to the generator assembly 28. In an embodiment, the actuator 20 is operably coupled to the generator assembly 28 by a wireless link, such as without limitation, a radiofrequency or infrared link. In use, the clinician may interact with the user interface 25 to preview operational characteristics of the ablation device 601.

Generator assembly 28, according to various embodiments, includes a generator module (e.g., 86 shown in FIG. 10) in operable communication with a processor (e.g., 82 shown in FIG. 10), a user interface 25, and an actuator 20. Ablation device 601 is operably coupled to an energy output of the generator module, which may be configured as a source of RF and/or microwave energy. Actuator 20 is operably coupled to the processor via the user interface 25. In embodiments, actuator 20 may be operably coupled to the processor and/or to the generator module by a cable connection or a wireless connection.

User interface 25 may include a display 21, such as without limitation a flat panel graphic LCD (liquid crystal display), adapted to visually display at least one user interface element 23, 24. In an embodiment, display 21 includes touchscreen capability (not shown), e.g., the ability to receive input from an object in physical contact with the display, such as without limitation, a stylus or a user's fingertip. A user interface element 23, 24 may have a corresponding active region, such that, by touching the screen within the active region associated with the user interface element, an input associated with the user interface element 23, 24 is received by the user interface 25.

User interface 25 may additionally, or alternatively, include one or more controls 22 that may include without limitation a switch (e.g., pushbutton switch, toggle switch, slide switch) and/or a continuous actuator (e.g., rotary or linear potentiometer, rotary or linear encoder). In an embodiment, a control 22 has a dedicated function, e.g., display contrast, power on/off, and the like. Control 22 may also have a function that may vary in accordance with an operational mode of the electrosurgical system 1000. A user interface element 23 may be positioned substantially adjacently to control 22 to indicate the function thereof. Control 22 may also include an indicator, such as an illuminated indicator, e.g., a single- or variably-colored LED indicator.

Figure 10:
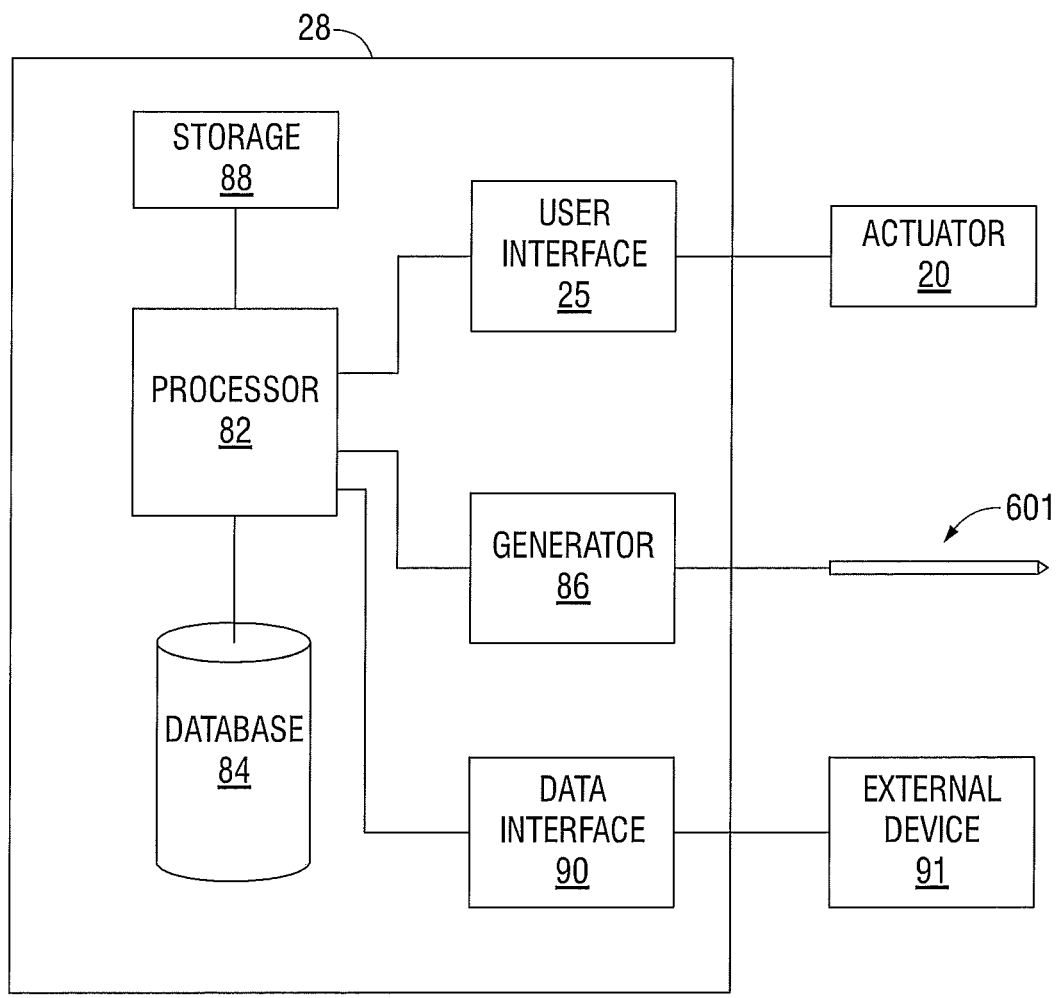
FIG. 10 is a block diagram of a microwave ablation system in accordance with the present disclosure.

FIG. 10 is a block diagram showing one embodiment of the electrosurgical system 1000 of FIG. 9. In an embodiment, the generator module 86 is configured to provide energy of about 915 MHz. Generator module 86 may additionally, or alternatively, be configured to provide energy of about 2450 MHz (2.45 GHz). The present disclosure contemplates embodiments wherein the generator module 286 is configured to generate a frequency other than about 915 MHz or about 2450 MHz, and embodiments wherein the generator module 86 is configured to generate variable frequency energy. Generator assembly 28 includes a processor 82 that is operably coupled to the user interface 25. Processor 82 may include any type of computing device, computational circuit, or any type of processor or processing circuit capable of executing a series of instructions that are stored in a memory, e.g., storage device 88 or external device 91.

In some embodiments, a storage device 88 is operably coupled to the processor 82, and may include random-access memory (RAM), read-only memory (ROM), and/or non-volatile memory (NV-RAM, Flash, and disc-based storage.) Storage device 88 may include a set of program instructions executable on the processor 82 for executing a method for displaying and controlling ablation patterns in accordance with the present disclosure. Generator assembly 200 may include a data interface 90 that is configured to provide a communications link to an external device 91. In some embodiments, the data interface 90 may be any of a USB interface, a memory card slot (e.g., SD slot), and/or a network interface (e.g., 100BaseT Ethernet interface or an 802.11 "Wi-Fi" interface.) External device 91 may be any of a USB device (e.g., a memory stick), a memory card (e.g., an SD card), and/or a network-connected device (e.g., computer or server).

Figure 11:
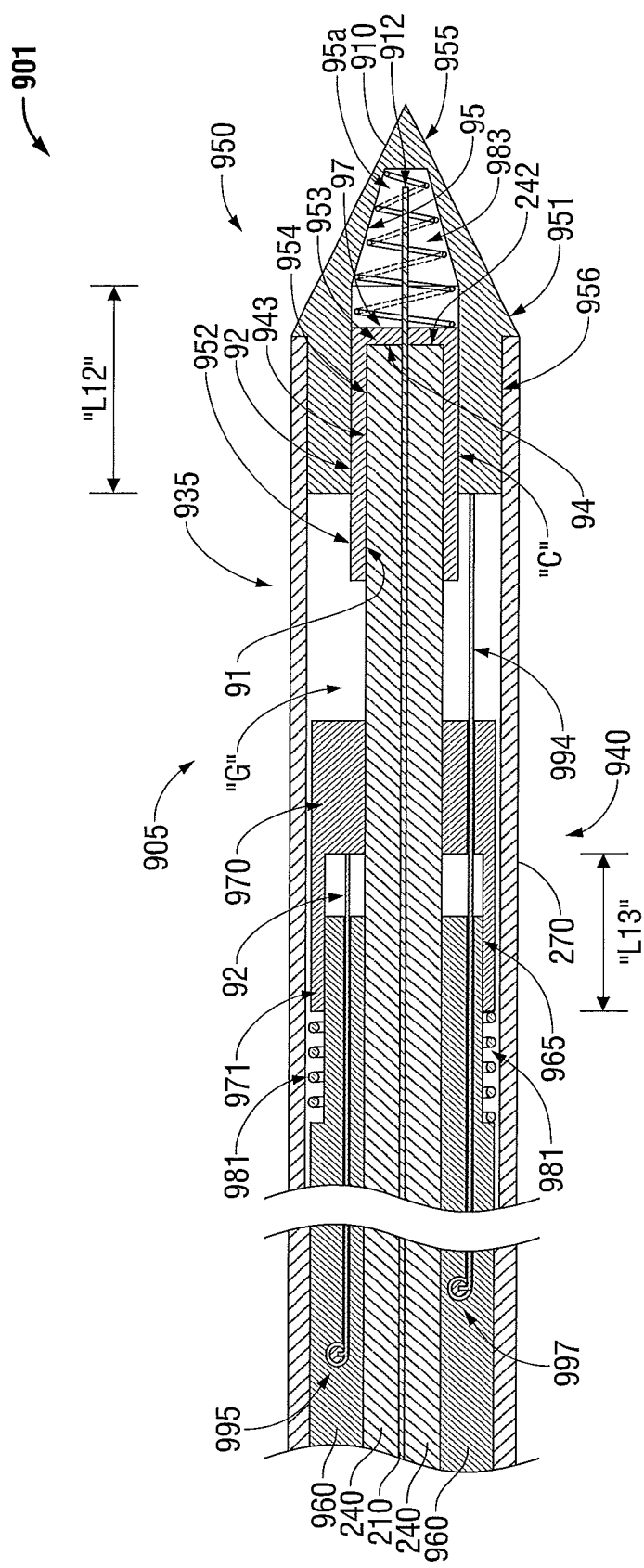
FIG. 11 is a partial, cross-sectional view of another embodiment of an ablation device in accordance with the present disclosure.

Generator assembly 28 may also include a database 84 that is configured to store and retrieve energy applicator data, e.g., parameters associated with one or energy applicators (e.g., 901 shown in FIG. 11). Parameters stored in the database 84 in connection with an energy applicator, or energy applicator array assembly, may include, but are not limited to, energy applicator (or applicator array assembly) identifier, energy applicator (or applicator array assembly) dimensions, a frequency, an ablation length (e.g., in relation to a radiating section length), an ablation diameter, a gap distance at the feed point (e.g. in relation to an ablation geometry), a temporal coefficient, a shape metric, and/or a frequency metric. In an embodiment, ablation pattern topology may be included in the database 84, e.g., a wireframe model of an applicator array assembly and/or an ablation pattern associated therewith.

Database 84 may also be maintained at least in part by data provided by the external device 91 via the data interface 90. For example without limitation, energy applicator data may be uploaded from an external device 91 to the database 84 via the data interface 90. Energy applicator data may additionally, or alternatively, be manipulated, e.g., added, modified, or deleted, in accordance with data and/or instructions stored on the external device 91. In an embodiment, the set of energy applicator data represented in the database 84 is automatically synchronized with corresponding data contained in the external device 91 in response to the external device 91 being coupled (e.g., physical coupling and/or logical coupling) to the data interface 90.

Processor 82 according to various embodiments is programmed to enable a user, via the user interface 25 and/or the display 21, to view at least one ablation pattern and/or other energy applicator data corresponding to an embodiment of an applicator array assembly. For example, a surgeon may determine that a substantially spherical ablation pattern is necessary. The surgeon may activate a "select ablation shape" mode of operation for generator assembly 28, preview an energy applicator array by reviewing graphically and textually presented data on the display 21, optionally, or alternatively, manipulate a graphic image by, for example, rotating the image, and select an array of energy applicators based upon displayed parameters. The selected energy applicator(s) may then be electrically coupled to the generator assembly 28 for use therewith.

In an embodiment, a surgeon may input via the user interface 25 an applicator array parameter to cause the generator assembly 28 to present one or more electromagnetic energy delivery devices corresponding thereto. For example, a surgeon may require a 3.0 cm×3.0 cm×3.0 cm ablation pattern, and provide an input corresponding thereto. In response, the generator assembly 28 may preview a corresponding subset of available electromagnetic energy delivery devices that match or correlate to the inputted parameter.

In an embodiment, a surgeon may input via the user interface 25 a selected power output, and the electrosurgical system 1000 controls the ablation device 601 to automatically thread out, or thread in, the outer sleeve 358 of the length adjustment member 350 to adjust the length of the distal radiating section 305, e.g., to adjust the ablation field radiated into tissue. Electrosurgical system 1000 may automatically thread out, or thread in, the outer sleeve 358 to adjust the length of the distal radiating section 305 based on the power level and/or level of reflected power.

Electrosurgical system 1000 may additionally, or alternatively, be adapted to control the ablation device 601 to automatically adjust the gap adjustment member 640 to shorten, or lengthen, the gap distance of the feed point 635. Electrosurgical system 1000 according to various embodiments may include a feedback looping mechanism suitable for use in controlling an embodiment of an ablation device (e.g., 601 shown in FIG. 6 or 901 shown in FIG. 11). The feedback looping mechanism may include, without limitation, proximity sensors, a voltage divider network, radial sensors, and/or feedback clicks, e.g., based upon the thread ratio of the threads 357a, 358a.

In another embodiment, the electrosurgical system 1000 may be adapted to control the ablation device 901 (shown in FIG. 11), and may include a first actuator (e.g., operably coupled to a first pivot element of the ablation device 901) and/or a second actuator (e.g., operably coupled to a second pivot element of the ablation device 901) to allow for automatic adjustment of the ablation field radiated into tissue. As described in more detail later in this disclosure, a first actuator may be used to automatically adjust an ablation field by adjusting the length of a distal radiating section using a length adjustment member (e.g., 950 shown in FIG. 11), and/or a second actuator may be used to adjust an ablation field by adjusting the gap distance of a feed point using a gap adjustment member (e.g., 940 shown in FIG. 11).

FIG. 11 shows a portion of an ablation device 901 according to another embodiment of the present disclosure including a distal radiating section 905, a length adjustment member 950 adapted to allow for dimensional adjustment of the distal radiating section 905. Ablation device 901 may additionally, or alternatively, include a gap adjustment member 940 adapted to allow for selective adjustment of the gap distance of a feed point 935. As shown in FIG. 11, the ablation device 901 generally includes an inner conductor 210 having a proximal end 912, a dielectric material 240 disposed coaxially around the inner conductor 210, an outer conductor 960 disposed coaxially around at least a proximal portion of the dielectric material 240. In some embodiments, the inner conductor 210 is formed from a first electrically-conductive material (e.g., stainless steel) and the outer conductor 260 is formed from a second electrically-conductive material (e.g., copper). Inner conductor 210 may be electrically coupled to the length adjustment member 950.

Length adjustment member 950 according to various embodiments includes an inner sleeve 952 having an inner surface 91 disposed about a proximal portion 943 of dielectric material (e.g., dielectric material 240 or other dielectric including without limitation, plastic ceramic or air), and an outer sleeve 951 disposed around at least a portion of an outer surface 92 of the inner sleeve 952. Outer sleeve 951 and the inner sleeve 952 may be formed of any suitable electrically-conductive material, e.g., metal such as stainless steel, titanium, etc. Outer sleeve 951 and the inner sleeve 952 may be of different sizes, diameters and thickness. The shape and size of the outer sleeve 951 and the inner sleeve 952 may be varied from the configuration depicted in FIG. 11.

In some embodiments, the inner sleeve 952 includes a hollow body 954, e.g., having a substantially cylindrical or tubular shape, and an end cap 953 adapted to close an open end of the hollow body. End cap 953 includes an inner surface 95 and an outer surface 97, and may have a generally circular or disc-like shape. As shown in FIG. 11, the end cap 953 may be provided with an aperture configured to allow passage of the proximal end 912 of the inner conductor 210 therethrough. In some embodiments the inner conductor 210 is electrically coupled to the end cap 953.

As shown in FIG. 11, the outer sleeve 951 may include a tubular body 956 defining a chamber "C", e.g., configured to receive at least a portion of the inner sleeve 952, and a tapered end portion 955 extending distally of a distal end of the sleeve body 956. In some embodiments, the tapered end portion 955 includes an inner surface 95 and an inner cavity 95a defined by the inner surface 95. As shown in FIG. 11, the inner cavity 95a may include an open end in communication with the chamber "C". The shape and size of chamber "C" and the cavity 95a may be varied from the configuration depicted in FIG. 11.

Length adjustment member 950 according to various embodiments includes a first biasing member 983. First biasing member 983 may be any suitable biasing member, e.g., a spring. First biasing member 983 may be configured to fit within the chamber "C" and/or the cavity 95a. In some embodiments, the first biasing member 983 is adapted to exert a biasing force against a proximal wall of the cavity 95a. In some embodiments, the distal end 242 of the dielectric material 240 may be disposed adjacent to the inner surface 94 of the end cap 953 to help prevent or minimize movement of the inner sleeve 952, proximally, e.g., when a force is exerted on the outer surface 97 of the end cap 953. As shown in FIG. 11, the first biasing member 983 may include an interior open space (e.g., defined by coils of a spring) configured to allow the conductor 210 to extend distally from the outer surface 97 of the end cap 953 into the chamber "C" and/or the cavity 95a. First biasing member 983 according to various embodiments is adapted to exert a biasing force sufficient to cause the outer sleeve 951 to move, distally, a length "L12". In some embodiments, the distance "L12" is in the range of about 3 cm to about 10 cm.

In some embodiments, where the first biasing member 983 is a coil spring, the biasing force may be a function of material properties and/or specific configuration of the spring, e.g., diameter of the spring wire, coil length and number of turns per unit length. In an embodiment, the first biasing member 983 is formed of a material having a known coefficient of thermal expansion, e.g., to allow for adjusting of the biasing force through the application of heat to the first biasing member 983.

As shown in FIG. 11, the outer sleeve 951 may be operably associated with a first tensioning element 994, e.g., a cable, coupled to a first pivot element 997, e.g., a pin and spool mechanism. In some embodiments, the length adjustment member 950 can be made longer or shorter by rotating the first pivot element 997. In some embodiments, when the first pivot element 997 is turned in a first rotational direction (e.g., clockwise), the first tensioning element 994 winds upon the first pivot element 997, causing the outer sleeve 951 to move proximally, and when the first pivot element 997 is turned in a second rotational direction opposite the first rotational direction (e.g., counter-clockwise) the first tensioning element 994 unwinds from the first pivot element 997, allowing the outer sleeve 951 to move, distally, in accordance with the biasing force exerted by the first biasing member 983 onto the outer sleeve 951. First tensioning element 994 may be formed from a material that is substantially transparent or semi-transparent to radiofrequency (RF) energy, e.g., TEFLON®, or any rigid dielectric material.

Gap adjustment member 940 according to various embodiments includes an axially slideable, outer-conductor sleeve element 970 having a proximal sleeve portion 971 disposed around a distal portion 965 of the outer conductor 960, and a second biasing member 981 adapted to exert a biasing force against the proximal sleeve portion 971. Second biasing member 981 may be any suitable biasing member, e.g., a spring. In some embodiments, the second biasing member 981 is adapted to exert a biasing force sufficient to cause the outer-conductor sleeve element 970 to move, distally, a length "L13". In some embodiments, the distance "L13" is about 1 cm.

Outer-conductor sleeve element 970 according to various embodiments may be operably associated with a second tensioning element 92, e.g., a cable, coupled to a second pivot element 995, e.g., a pin and spool mechanism. In some embodiments, the gap adjustment member 940 can be positioned, e.g., in relation to the distal end of the outer conductor 960, by rotating the second pivot element 995. In some embodiments, when the second pivot element 995 is turned in a first rotational direction (e.g., clockwise), the second tensioning element 92 winds upon the second pivot element 995, causing the outer-conductor sleeve element 970 to move proximally, and when the second pivot element 995 is turned in a second rotational direction opposite the first rotational direction (e.g., counter-clockwise) the second tensioning element 92 unwinds from the second pivot element 995, allowing the outer-conductor sleeve element 970 to move, distally, in accordance with the biasing force exerted by the second biasing member 981 onto the outer-conductor sleeve element 970. Second tensioning element 92 may be formed from a material that is substantially transparent or semi-transparent to RF energy, e.g., TEFLON®, or any rigid dielectric material.

Ablation device 901 according to embodiments of the present disclosure may include a first actuator (e.g., 1197 shown in FIG. 13) operably coupled to the first pivot element 997 for controlling the length adjustment member 950 in an automatic process. In some embodiments, the first actuator is operably associated with a controller (e.g., processor 82 of the electrosurgical system 1000). Ablation device 901 may additionally, or alternatively, include a second actuator (e.g., 1195 shown in FIG. 13) operably coupled to the second pivot element 995 for controlling the gap adjustment member 940 in an automatic process.

Figure 12:
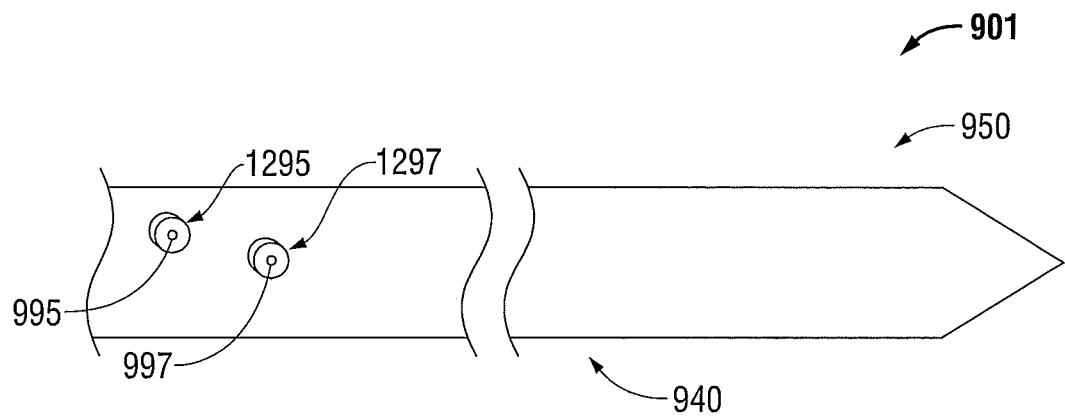
FIG. 12 is a partial, perspective view of the ablation device of FIG. 11 shown with a first operating element and a second operating element.

As shown in FIG. 12, the ablation device 901 may include a first operating element 1297, e.g. a knob or button, operably coupled to the first pivot element 997. In some embodiments, the first operating element 1297 (hereinafter referred to as first knob 1297) allows a user to manually adjust the length adjustment member 950 by turning the first knob 1297 in a first rotational direction (e.g., clockwise), which may wind the first tensioning element 994 upon the first pivot element 997, e.g., causing the outer sleeve 951 to move proximally, and/or by turning the first knob 1297 in a second rotational direction (e.g., counter-clockwise), which may unwind the first tensioning element 994 from the second pivot element 995, e.g., allowing the outer sleeve 951 to move distally. First knob 1297 may have a variety of shapes, textures and colors. In some embodiments, the first knob 1297 has a substantially cylindrical shape.

Ablation device 901 may additionally, or alternatively, include a second operating element 1295, e.g. a knob or button, operably coupled to the second pivot element 995. In some embodiments, the second operating element 1295 (hereinafter referred to as second knob 1295) may allow a user to manually adjust the gap adjustment member 940 by turning the second knob 1295 in a first rotational direction (e.g., clockwise), which may wind the second tensioning element 92 upon the second pivot element 995, e.g., causing the outer-conductor sleeve element 970 to move proximally, and/or by turning the second knob 1295 in a second rotational direction (e.g., counter-clockwise), which may unwind the second tensioning element 92 from the from the second pivot element 995, e.g., allowing the outer-conductor sleeve element 970 to move distally. The shape and size of the first knob 1297 and the second knob 1295 may be varied from the configuration depicted in FIG. 12.

Figure 13:
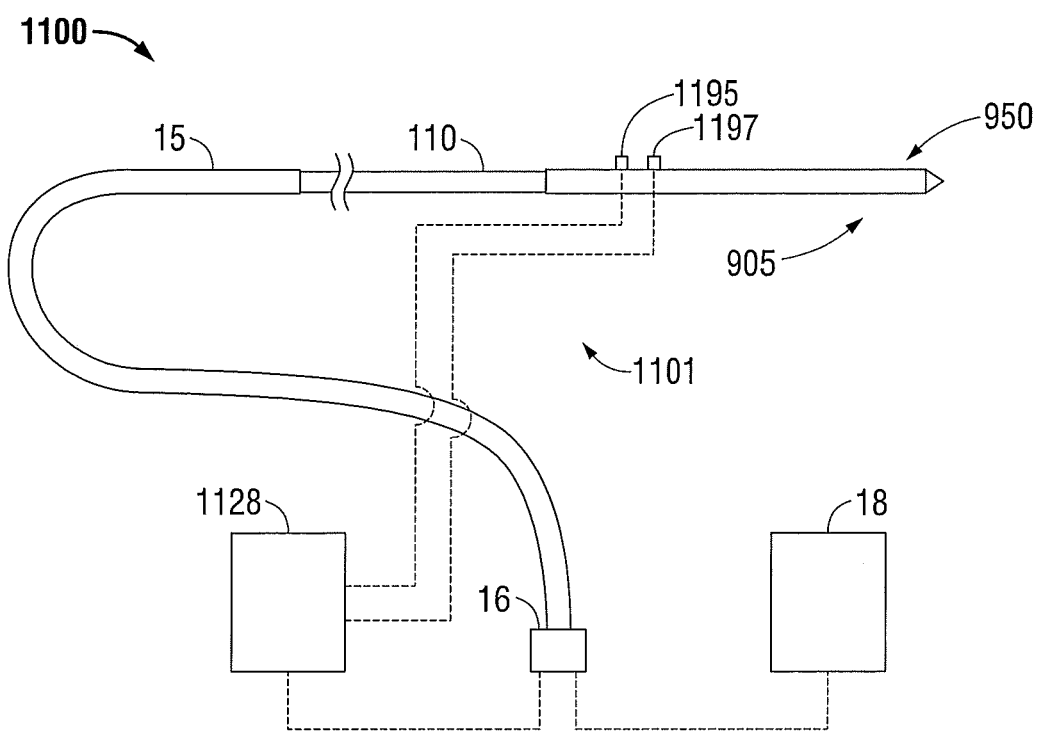
FIG. 13 is a schematic diagram of an ablation system including the ablation device of FIG. 11 according to an embodiment of the present disclosure.

FIG. 13 shows an electrosurgical system 1100 according to an embodiment of the present disclosure including an ablation device or probe 1101 having a radiating section 905. Probe 1101 includes a radiation field adjustment member (e.g., length adjustment member 950 and/or gap adjustment member 940 shown in FIG. 11) adapted to allow for selective adjustment of the ablation field radiated about the radiating section into tissue. Probe 1101 according to various embodiments is similar to the probe 901 of FIG. 11, except for a first actuator 1197 and a second actuator 1195. In some embodiments, the first actuator 1197 is operably coupled to a first pivot element 997 (shown in FIG. 11), and/or the second actuator 1195 is operably coupled to a second pivot element 995 (shown in FIG. 11). In some embodiments, the first actuator 1197 and/or the second actuator 1195 may be electrically coupled to a generator assembly 1128. First actuator 1197 and the second actuator 1195 may allow for automatic adjustment of a length adjustment member 950 (shown in FIG. 11) and a gap adjustment member 940 (shown in FIG. 11), respectively, e.g., in connection with a process running on a processor 82 (shown in FIG. 10).

Generator assembly 1128 according to various embodiments is configured to enable a user, via a user interface 25 (shown in FIG. 9) and/or a display 21 (shown in FIG. 9), to view at least one ablation pattern and/or other energy applicator data corresponding to the probe 1101. Generator assembly 1128 is generally similar to the generator assembly 28 of FIGS. 9 and 10, and further description thereof is omitted in the interests of brevity.

In some embodiments, a surgeon may input via the user interface 25 a selected power output, and the electrosurgical system 1100 controls the actuator 1197 to automatically adjust the length adjustment member 950, to adjust the length of the distal radiating section 905, based on the power level and/or level of reflected power. As cooperatively shown in FIGS. 11 and 13, the presently disclosed electrosurgical system 1100 may control the actuator 1197 to turn the first pivot element 997 in a first rotational direction, wherein the first tensioning element 994 may wind upon the first pivot element 997, causing the outer sleeve 951 of the length adjustment member 950 to move proximally, and/or turn the first pivot element 997 in a second rotational direction, wherein the first tensioning element 994 may unwind from the first pivot element 997, allowing the outer sleeve 951 to move distally, in accordance with the biasing force exerted by the first biasing member 983 onto the outer sleeve 951.

Electrosurgical system 1100 may additionally, or alternatively, be adapted to control the second actuator 1195 to automatically adjust the gap adjustment member 940, to shorten or lengthen the gap distance of the feed point. As cooperatively shown in FIGS. 11 and 13, the presently disclosed electrosurgical system 1100 may control the actuator 1195 to turn the second pivot element 995 in a first rotational direction, wherein the second tensioning element 92 may wind upon the second pivot element 995, causing the outer-conductor sleeve element 970 to move proximally, and/or turn the second pivot element 995 in a second rotational direction, wherein the second tensioning element 92 may unwind from the second pivot element 995, allowing the outer-conductor sleeve element 970 to move distally, e.g., in accordance with the biasing force exerted by the second biasing member 981 onto the outer-conductor sleeve element 970.

First actuator 1197 and/or the second actuator 1195 may include a pneumatic actuator, a hydraulic actuator, an electric actuator, or other suitable actuator. In some embodiments, the first actuator 1197 is a rotary electric actuator. In some embodiments, the second actuator 1195 is a rotary electric actuator.

Hereinafter, a method of directing energy to tissue, in accordance with the present disclosure, is described with reference to FIG. 14, and a method of adjusting an ablation field radiating into tissue is described with reference to FIG. 15. It is to be understood that the steps of the methods provided herein may be performed in combination and in a different order than presented herein without departing from the scope of the disclosure.

Figure 14:
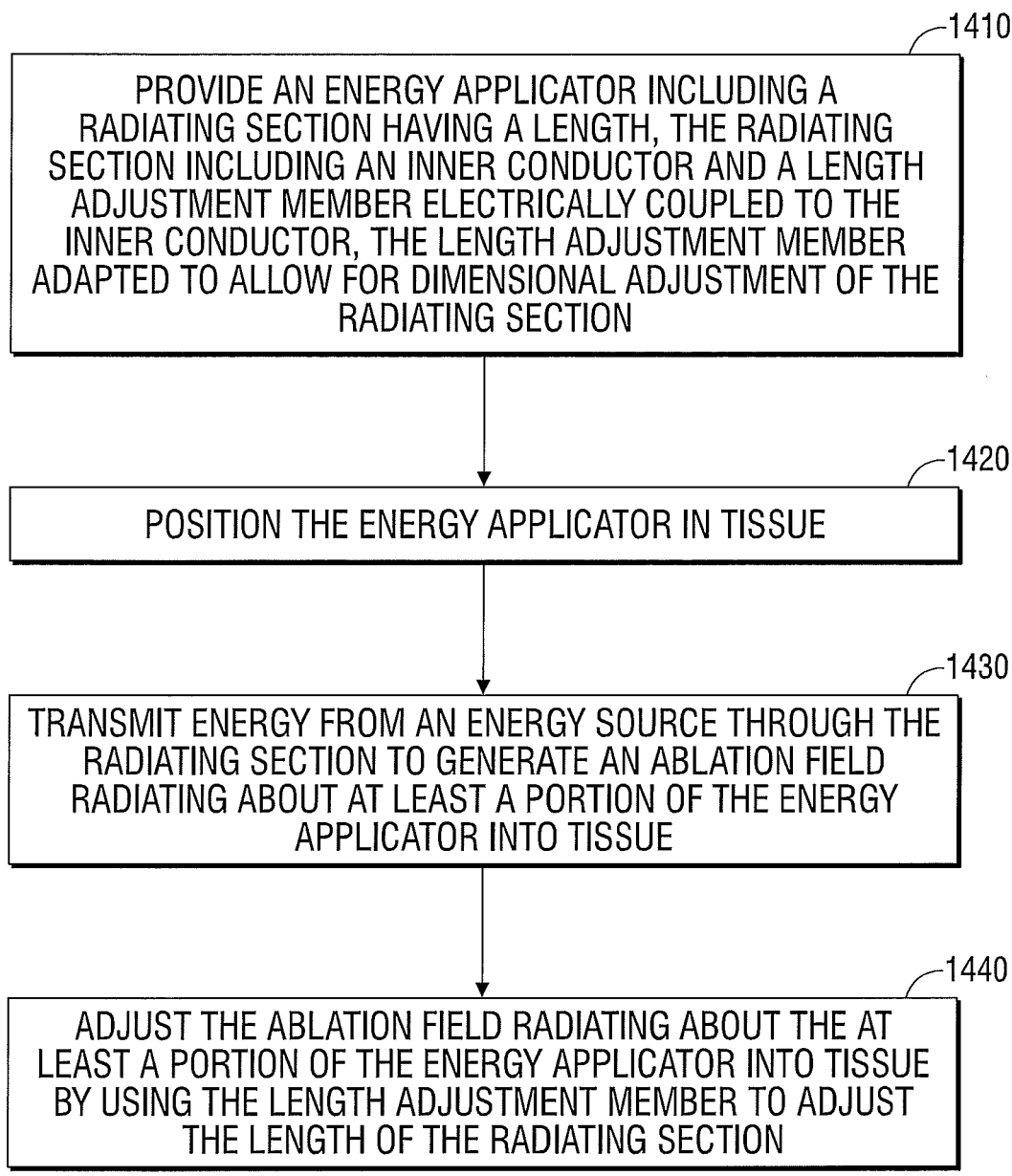
FIG. 14 is a flowchart illustrating a method of directing energy to tissue according to an embodiment of the present disclosure.

FIG. 14 is a flowchart illustrating a method of directing energy to tissue according to an embodiment of the present disclosure. In step 1410, an energy applicator (e.g., 100 shown in FIG. 1) is provided. The energy applicator includes a radiating section (e.g., 150 shown in FIG. 2A) having a length (e.g., "L1" shown in FIG. 2A). The radiating section includes an inner conductor (e.g., 210 shown in FIGS. 2A and 2B) and a length adjustment member (e.g., 250 shown in FIGS. 2A and 2B) that is electrically coupled to the inner conductor. Inner conductor 210 may be formed from a yieldable or flexible, electrically-conductive material, e.g., titanium. The length adjustment member is adapted to allow for dimensional adjustment of the radiating section, and may include a sleeve portion (e.g., 255 shown in FIG. 2A). An insulator sleeve (e.g., 270 shown in FIGS. 2A and 2B) may be disposed around at least a portion of an outer conductor (e.g., 260 shown in FIGS. 2A and 2B) of the energy applicator. The insulator sleeve may extend distally beyond the distal end of the outer conductor, e.g., to enhance slideability and/or repositionability of the sleeve portion. In some embodiments, the radiating section is configured for radiating energy in a broadside radiation pattern.

In step 1420, the energy applicator (e.g., 100 shown in FIG. 1) is positioned in tissue. The energy applicator may be inserted directly into tissue, inserted through a lumen, e.g., a vein, needle, endoscope or catheter, placed into the body during surgery by a clinician, or positioned in the body by other suitable methods known in the art. The energy applicator may be configured to operate with a directional radiation pattern.

In step 1430, energy is transmitted from an energy source (e.g., 28 shown in FIG. 1) through the radiating section (e.g., 150 shown in FIG. 2A) to generate an ablation field radiating about at least a portion of the energy applicator into tissue. The energy source may be any suitable electrosurgical generator for generating an output signal. In some embodiments, the energy source is a microwave energy source, and may be configured to provide microwave energy at an operational frequency from about 300 MHz to about 10 GHz.

In step 1440, the ablation field is adjusted by using the length adjustment member to adjust the length of the radiating section. In some embodiments of the presently disclosed energy applicators, the ablation field may be adjusted by using a gap adjustment member (e.g., 940 shown in FIG. 11) adapted to allow for selective adjustment of the gap distance of a feed point (e.g., 935 shown in FIG. 11).

Figure 15:
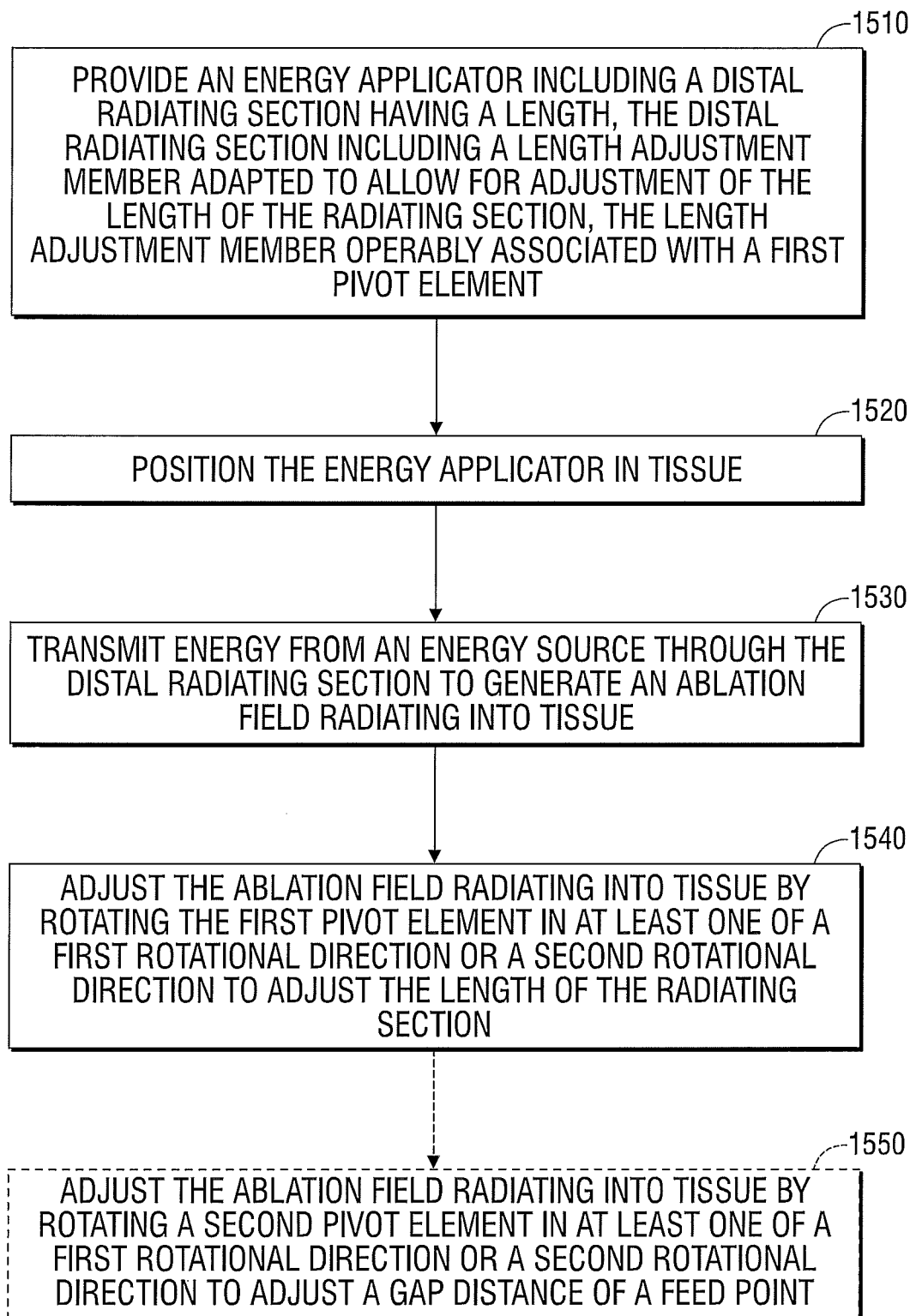
FIG. 15 is a flowchart illustrating a method of adjusting an ablation field radiating into tissue.

FIG. 15 is a flowchart illustrating a method of adjusting an ablation field radiating into tissue according to an embodiment of the present disclosure. In step 1110, an energy applicator (e.g., 901 shown in FIG. 11) is provided. The energy applicator includes a distal radiating section (e.g., 905 shown in FIG. 11) having a length. The distal radiating section includes a length adjustment member (e.g., 950 shown in FIG. 11) adapted to allow for selective adjustment of the length of the distal radiating section. The length adjustment member is operably associated with a first pivot element (e.g., 997 shown in FIG. 11).

In step 1520, the energy applicator (e.g., 901 shown in FIG. 11) is positioned in tissue. The energy applicator may be positioned in tissue by any suitable method.

In step 1530, energy is transmitted from an energy source (e.g., 28 shown in FIG. 1) through the distal radiating section (e.g., 905 shown in FIG. 11) to generate an ablation field radiating into tissue. In some embodiments, the energy source is a microwave energy source, and may be configured to provide microwave energy at an operational frequency from about 300 MHz to about 10 GHz.

In step 1540, the ablation field radiating into tissue is adjusted by rotating the first pivot element (e.g., 997 shown in FIG. 11) in a first rotational direction or a second rotational direction to adjust the length of the radiating section. The first pivot element may be rotated manually, e.g., using a first knob (e.g., 1297 shown in FIG. 12), or automatically, e.g., by an actuator (e.g., 1297 shown in FIG. 13) electrically coupled to a generator assembly (e.g., 1128 shown in FIG. 13).

Additionally, the energy applicator (e.g., 901 shown in FIG. 11) may include a gap adjustment member (e.g., 940 shown in FIG. 11) adapted to allow for selective adjustment of the gap distance of a feed point. Optionally, in a step 1550, the ablation field radiating into tissue may be adjusted by rotating a second pivot element (e.g., 995 shown in FIG. 11) to adjust the gap distance of the feed point. The second pivot element may be rotated manually, e.g., using a second knob (e.g., 1295 shown in FIG. 12), or automatically, e.g., by an actuator (e.g., 1295 shown in FIG. 13) electrically coupled to a generator assembly (e.g., 1128 shown in FIG. 13).

The above-described ablation devices including a length adjustment member adapted to allow for dimensional adjustment of a radiating section and/or a gap adjustment member adapted to allow for selective adjustment of the gap distance of a feed point and methods of directing electromagnetic radiation to tissue according to embodiments of the present disclosure may allow clinicians to avoid ablating or unnecessarily heating tissue structures, such as large vessels, healthy organs or vital membrane barriers, by adjusting the ablation field radiating into tissue. The above-described ablation devices may be suitable for use in open surgical, endoscopic (e.g., rigid or flexible), or percutaneous procedures.

The above-described electrosurgical systems may enable a user to view one or more ablation patterns and/or other energy applicator data corresponding to an embodiment of an ablation device, which may allow clinicians to predict ablation volume, avoid complications, and/or plan for treatment margins. The above-described electrosurgical systems may be adapted to automatically adjust the length of the radiating section using an embodiment of the presently disclosed length adjustment members and/or the gap distance at the feedpoint using an embodiment of the presently disclosed gap adjustment members.

The above-described ablation devices may be designed to operate at about 915 MHz, about 2.45 GHz, or any other applicable frequency. In some embodiments, the presently disclosed ablation devices including a length adjustment member adapted to allow for dimensional adjustment of a radiating section and/or a gap adjustment member adapted to allow for selective adjustment of the gap distance of a feed point, and electrosurgical systems including the same, may be operated at a first frequency, e.g., about 915 MHz, wherein the distal radiating section has a first length, e.g., about 2 cm, and a second frequency, e.g., about 2.45 GHz, wherein the distal radiating section is adjusted to have a second length, e.g., about 1 cm.

The above-described ablation devices with adjustable radiating section lengths may be suitable for use in surgical or non-surgical (e.g., interventional radiology, etc.) settings.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical system, comprising:
   a generator; and
   an ablation device including:
      a feedline including an inner conductor, an outer conductor coaxially-disposed around the inner conductor, and a dielectric material disposed therebetween;
      a radiating section operably coupled to the feedline, the radiating section defining a longitudinal axis; and
      a radiation field adjustment member adapted to allow for selective adjustment of the ablation field radiated about the radiating section into tissue, the radiation field adjustment member including:
         a length adjustment member including an inner sleeve and an outer sleeve disposed around at least a portion of the inner sleeve, the outer sleeve operably associated with a first pivot element configured to translate the outer sleeve along the longitudinal axis defined by the radiating section;
         a gap adjustment member disposed proximal of the length adjustment member and configured to selectively adjust a gap distance defined between a distal end of the outer conductor and a proximal end of the radiating section; and
         a first actuator operably coupled to the first pivot element and configured to turn the first pivot element in at least one of a first rotational direction or a second rotational direction.

2. The system of claim 1, wherein when the first actuator turns the first pivot element in the first rotational direction a first tensioning element winds upon the first pivot element, causing the outer sleeve to move proximally.

3. The system of claim 1, wherein when the first actuator turns the first pivot element in the second rotational direction a first tensioning element unwinds from the first pivot element, allowing the outer sleeve to move distally.

4. The system of claim 1, wherein the gap adjustment member includes an axially slideable, outer-conductor sleeve element having a proximal sleeve portion disposed around a distal portion of the outer conductor.

5. The system of claim 4, wherein the gap adjustment member further includes a second pivot element and a second tensioning element, the second tensioning element coupled to the second pivot element and operably associated with the outer-conductor sleeve element.

6. The system of claim 5, wherein the radiation field adjustment member further includes a second actuator operably coupled to the second pivot element, the second actuator configured to turn the second pivot element in at least one of a first rotational direction or a second rotational direction.

7. The system of claim 6, wherein, when the second actuator turns the second pivot element in the first rotational direction, the second tensioning element winds upon the second pivot element, causing the outer-conductor sleeve to move proximally.

8. The system of claim 6, wherein, when the second actuator turns the second pivot element in the second rotational direction, the second tensioning element unwinds from the second pivot element, allowing the outer-conductor sleeve to move distally.

9. An electrosurgical system, comprising:
a generator including a processor; and
an ablation device including:
- a feedline including an inner conductor, an outer conductor coaxially-disposed around the inner conductor, and a dielectric material disposed therebetween;
- a radiating section operably coupled to the feedline; and
- a radiation field adjustment member adapted to allow for selective adjustment of the ablation field radiated about the radiating section into tissue, wherein the radiation field adjustment member includes:
  - an inner sleeve;
  - an outer sleeve disposed around at least a portion of the inner sleeve and operably associated with a first pivot element;
  - a biasing member disposed between the inner and outer sleeves and configured to move the outer sleeve longitudinally with respect to the inner sleeve; and
  - a first actuator electrically coupled to the processor, the processor configured to control the first actuator to turn the first pivot element in at least one of a first rotational direction or a second rotational direction.

* * * * *